United States Patent
MacMillan et al.

(10) Patent No.: US 6,534,434 B2
(45) Date of Patent: Mar. 18, 2003

(54) CHIRAL IMIDAZOLIDINONE-BASED CATALYST COMPOSITION AND REACTION SYSTEM

(75) Inventors: David W. C. MacMillan, Berkeley, CA (US); Kateri A. Ahrendt, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/919,078

(22) Filed: Jul. 30, 2001

(65) Prior Publication Data

US 2002/0013475 A1 Jan. 31, 2002

Related U.S. Application Data

(60) Division of application No. 09/547,958, filed on Apr. 12, 2000, now Pat. No. 6,307,057, which is a continuation-in-part of application No. 09/484,082, filed on Jan. 18, 2000, now Pat. No. 6,369,243.

(51) Int. Cl.$^7$ .................. C07D 493/08; C07C 43/61; C07C 43/62
(52) U.S. Cl. .................. 502/167; 502/28; 548/316.4; 548/326.1; 549/469; 560/261; 568/445; 568/446
(58) Field of Search .................. 502/28.167; 548/316.4, 548/326.1; 549/469; 560/261; 568/445, 446

(56) References Cited

U.S. PATENT DOCUMENTS

| | | | |
|---|---|---|---|
| 4,324,884 A | 4/1982 | White et al. | 528/207 |
| 4,355,184 A | 10/1982 | Kaku et al. | 568/31 |
| 5,428,174 A | 6/1995 | Reissenweber et al. | 548/247 |
| 6,040,262 A | 3/2000 | Fougret et al. | 502/162 |

FOREIGN PATENT DOCUMENTS

| | | |
|---|---|---|
| JP | 63-195650 | 8/1988 |
| WO | WO 92/02505 | 2/1992 |

OTHER PUBLICATIONS

Bruice (1990), "Role of the Acidity of the Ketone in Determining the Mechanism of Enolization via Proton Abstraction from Ketone, Carbinolamine, or Imine. Catalysis of the Enolization of 2,4–Pentanedione and 3–Methyl–2, 4–Pentanedione by Oxyanions and by Primary, Secondary, and Tertiary Amines," *J. Am. Chem. Soc.* 112:7361–7368.

Coward et al. (1969), "Intramolecular Amine–Catalyzed Ketone Enolization. A Search for Concerted Intramolecular General–Base, General–Acid Catalysis," *Journal of the American Chemical Society* 91(19): 5339–5345.

Demir et al. (1996), "Enantioselective Synthesis of 4–Hydroxy–3–)3–Oxo–1–Phenyl Butyl)–2H–1–Benzopyran–2–One (Warfarin)," *Tr. J. of Chemistry* 20:139–145.

Gothelf et al. (1998), "Asymmetric 1,3–Dipolar Cycloaddition Reactions," *Chem. Rev.* 98:863–909.

Guerin et al. (1999), "Amine–Catalyzed Addition of Azide Ion to α,β–Unsaturated Carbonyl Compounds," *Organic Lettters* 1(7):1107–1109.

Heinz et al. (1995), "1–(1–Naphthyl)ethylamine and Derivatives Thereof as Chiral Modifiers in the Enantioselective Hydrogenation of Ethyl Pyruvate Over Pt–Alumina," *J. Chem. Soc., Chem. Commun.*, pp. 1421–1422.

Hubbard et al. (1998), "Mechanism of Amine–Catalyzed Ester Formation From an Acid Chloride and Alcohol," *J. Org. Chem.* 63(3):677–683.

Hubert et al. (1998), *Chemical Abstracts* 129:81689.

Ishihara et al. (1994), "Bronsted Acid Assisted Chiral Lewis Acid (BLA) Catalyst for Asymmetric Diels–Alder Reaction," *J. Am. Chem. Soc.* 116(4):1561–1562.

Ishihara et al. (1998), "Design of Bronsted Acid–Assisted Chiral Lewis Acid (BLA) Catalysts for Highly Enantioselective Diels–Alder Reactions," *J. Am. Chem. Soc.* 120(28):6920–6930.

Ishii et al. (1999), "Formation of 3–Hydroxyalkyl Carbamates from Carbon Dioxide, Amines and Oxetanes," *Synthetic Communications* 29:3207–3214.

Iwabuchi et al. (1999) "Chiral Amine–Catalyzed Asymmetric Baylis–Hillman Reaction: A Reliable Route to Highly Enantiomerically Enriched (α–Methylene–β–Hydroxy)Esters," *J. Am. Chem. Soc.* 121(43):10219–10220.

Kawara et al. (1994), "An Enantioselective Michael Addition of Soft Nucleophiles to Prochiral Enone Catalyzed by (2–Pyrrolidyl)Alkyl Ammonium Hydroxide," *Tetrahedron Letters* 35(47):8805–8808.

List et al. (200), "Proline–Catalyzed Direct Asymmetric Aldol Reactions," *J. Am. Chem. Soc.* 122(10):2395–2396.

Polonski (1985), *Chemical Abstracts* 103:70848.

Sasai et al. (1994), "Catalytic Asymmetric Michael Reactions Promoted by a Lithium–Free Lanthanum–BINOL Complex," *J. Am. Chem. Soc.* 116(4):1571–1572.

Sasai et al. (1995), "The First Heterobimetallic Multifunctional Asymmetric Catalyst," *J. Am. Chem. Soc.* 117(23):6194–6198.

(List continued on next page.)

Primary Examiner—Richard L. Raymond
(74) Attorney, Agent, or Firm—Diannne E. Reed; Reed & Associates

(57) ABSTRACT

Acid addition salts of imidazolidinones are provided as catalysts for transforming a functional group within a first reactant by reaction with a second reactant. Exemplary first reactants are α,β-unsaturated carbonyl compounds such as α,β-unsaturated ketones and α,β-unsaturated aldehydes. Chiral imidazolidinone salts can be used to catalyze enantioselective reactions, such that a chiral product is obtained from a chiral or achiral starting material in enantiomerically pure form.

36 Claims, 7 Drawing Sheets

OTHER PUBLICATIONS

Serebryakov et al. (1998), "The Effects of the Nature of Catalyst and of the Solvent on the Stereoselectivity in Amine–Catalyzed Asymmetric Synthesis of Substituted Cyclohexa–1,3–Dienes From Prenal and Monoesters of Ylidenemalonic Acids," *Russian Chemical Bulletin* 47(1):82–90.

Schuster et al. (2000), "Catalysis of a Diels–Alder Reaction by Amidinium Ions," *J. Org. Chem.* 65(6):1697–1701.

Shi et al. (1995), "Synthesis of Axially Dissymmetric Chiral Ammonium Salts by Quaternization of Secondary Amines with (R)–(+)–2, 2'–Bis(bromomethyl)–6, 6'–dinitrobiphenyl)–2, 1'–binaphthyl and an Examination of their Abilities as Chiral Phase–transfer Catalysts," *J. Chem. Research (S)*, pp. 46–47 (*J. Chem. Research (M)*, pp. 0401–0411.

Smissman et al. (1976), *Chemical Abstracts* 84:43932.

Solodin (1993), *Chemical Abstracts* 118:80859.

Solodin et al. (1991), *Chemical Abstracts* 114:101833.

Tanikaga et al. (1988), "Stereochemical Behavior of Intermediary Compounds in the Amine–Catalyzed Knoevenagel Reaction." *Bull. Chem. Soc. Jpn.* 61(9):3211–3216.

Yamaguchi et al. (1991), "The Michael Addition of Dimethyl Malonate to α,β–Unsaturated Aldehydes Catalysed by Proline Lithium Salt," *J. Chem. Soc., Chem. Commun.*, pp. 1088–1089.

Yamaguchi et al. (1993), "A Catalytic Enantioselective Michael Addition of a Simple Malonate to Prochrial α,β–Unsaturated Ketones and Aldehydes," *Angewandte Chemie International Edition* 32(8):1176–1178.

Yamagushi et al. (1996), "Asymmetric Michael Addition of Malonate Anions to Prochiral Acceptors Catalyzed by L–Proline Rubidium Salt," *J. Org. Chem.* 61(10):3520–3530.

Yamaguchi et al. (1997), "Asymmetric Michael Addition of Nitroalkanes to Prochiral Acceptors Catalyzed by Proline Rubidium Salts," *Tetrahedron* 53(32):11223–11236.

Yamaguchi et al. (1994), "Catalytic Asymmetric Michael Addition of Nitroalkane to Enone and Enal," *Tetrahedron Letters* 35(44):8233–8236.

Yang et al. (1998), "Design and Synthesis of Chiral Ketones for Catalytic Asymmetric Epoxidation of Unfunctionalized Olefins," *J. Am. Chem. Soc.* 120(24):5943–5952.

Zehavi et al. (1961), *Chemical Abstracts* 55:20979.

Cyclopropanation:

Epoxidation:

Intramolecular Cycloaddition:

[3 + 2] Cycloaddition:

Michael Addition of Furan:

Michael Addition of Nitromethane:

Two possible iminium ion intermediates, leading to two possible enantiomeric products:

exo (R) favored

Process Flow Block Diagram

US 6,534,434 B2

CHIRAL IMIDAZOLIDINONE-BASED CATALYST COMPOSITION AND REACTION SYSTEM

CROSS-REFERENCE TO RELATED APPLICATIONS

This is a divisional of U.S. patent application Ser. No. 09/547,958, filed Apr. 12, 2000, which issued on Oct. 23, 2001 as U.S. Pat. No. 6,307,057, which is a continuation-in-part of U.S. patent applicaiton Ser. No. 09/484,082, filed Jan. 18, 2000, which issued on Apr. 9, 2002 as U.S. Pat. No. 6,369,243, the disclosures of which are incorporated by reference herein.

TECHNICAL FIELD

The present invention relates to organic reagents and their use as catalysts for a variety of reactions. More particularly, this invention relates to the use of an acid addition salt of an imidazolidinone to catalyze various bond-forming reactions. The invention finds utility in the fields of organic synthesis and stereospecific catalysis.

BACKGROUND

Ancillary (or "spectator") ligand-metal coordination complexes (e.g. organometallic complexes) and compositions are useful as catalysts, stoichiometric reagents and therapeutic agents. The ancillary ligand contains functional groups that bind to one or more metal centers and remain associated therewith, providing an opportunity to modify the steric, electronic and chemical properties of the active sites of the complex, i.e., the metal centers.

Unfortunately, many organometallic reagents are expensive and depending on their catalytic activity may be not be commercially viable. Generally, organometallic catalysts require bidentate or polydentate ligands that are difficult to synthesize, requiring multiple reaction steps and increased cost. Due to their high sensitivity to oxygen, air and moisture, organometallic catalysts require the use of inert, nonaerobic conditions, both during synthesis and during catalysis and, once catalysis is complete, these catalysts are also problematic as they are difficult to recycle and are generally environmentally unsafe. The inherent toxicity of these compounds greatly reduces their usefulness in pharmaceutical applications. Moreover, many organometallic complexes are useful only for very specific chemical reactions and do not have broad utility as catalysts for a variety of different types of reactions. This problem may be emphasized for the catalysis of reactions leading to chiral molecules, particularly the conversion of either chiral or achiral molecules via enantioselective catalysis to provide a chiral product.

Over the last 30 years enantioselective catalysis has become one of the most important frontiers in exploratory organic synthetic research. In the pharmaceutical industry and other industries, the use of pure enantiomeric molecules is often important for safety and efficacy. Thus, in the production of pharmaceuticals, use of catalysts or reagents that preferentially produce one enantiomer of a molecule relative to another enantiomer is particularly advantageous. Unfortunately, the catalysts that produce such enantiomers are typically organometallic complexes that are specific for a particular reaction. In addition, there is no way to predict with any reasonable accuracy which enantiomer will result. Examples of organometallic catalysts used to prepare chiral materials include BINOL-based complexes (Mikami et al. (1994) *J. Am. Chem. Soc.* 116:2812; Kobayashi et al. (1994) *J. Am. Chem. Soc.* 116:4083; Mikami et al. (1989) *J. Am. Chem. Soc.* 111:1940; Mikami et al. (1994) *J. Am. Chem. Soc.* 116:4077; Keck et al. (1993) *J. Am. Chem. Soc.* 115:8467; Keck et al. (1995) *J. Am. Chem. Soc.* 117:2363), BINAP-based complexes (Miyashita et al. (1980) *J. Am. Chem. Soc.* 102:7932; Miyashita et al. (1984) *Tetrahedron* 40:1245; Takaya et al. (1986) *J. Org. Chem.* 51:629; Takaya et al. (1988) *Org. Synth.* 67:20; Cai et al. (1995) *Tetrahedron Lett..* 36:7991), DUPHOS complexes (Burk et al. (1990) *Organometallics* 9:2653; Burk et al. (1993) *J. Am. Chem. Soc.* 115:10125; Burk et al. (1992) *J. Am. Chem. Soc.* 114:6266; Burk et al. (1995) *J. Am. Chem. Soc.* 112:9375); salen-based complexes (i.e., organometallic complexes containing the N,N'-bis(3,5-di-t-butylsalicylidene)-1,2-cyclohexanediamino ligand; see, e.g., Li et al. (1993) *J. Am. Chem. Soc.* 115:5326, and Evans et al. (1993) *Tetrahedron Lett.* 34:7027), and bisoxazoline-containing compounds (Evans et al. (1993) *J. Am. Chem. Soc.* 115:6460; Evans et al. (1997) *J. Am. Chem. Soc.* 119:7893; Evans et al. (1996) *Tetrahedron Lett.* 37:7481; Corey et al. (1992) *Tetrahedron Lett.* 3:6807; Gothelf et al. (1996) *J. Org. Chem.* 61:346).

Despite the observed need and relatively few, narrow solutions, relatively few asymmetric transformations have been reported which employ organic molecules as reaction catalysts. There is tremendous potential for academic, economic and environmental benefit should versatile, chiral organic catalysts be developed. Only a few researchers have disclosed organic catalysts useful for preparing chiral materials. See, e.g., *Asymmetric Catalysis in Organic Synthesis,* Noyori, R., Ed. (New York: Wiley, 1994) and *Asymmetric Synthesis,* Ojima, I., Ed. (New York: VCH, 1993), and references cited therein. Also see Yang et al. (1998) *J. Am. Chem. Soc.* 120(24):5943–5952, who disclose the use of a dioxirane to catalyze enantioselective epoxidation, Shi et al. (1995) *J. Chem. Research (S)*:46–47 (*J. Chem. Research (M)*: 0401–0411), who disclose preparation of chiral quaternary ammonium salts stated to be useful as chiral phase-transfer catalysts by reaction of (R)-(+)-2,2'-bis(bromomethyl)-6,6'-dinitrobiphenyl and (R)-(+)-2,2'-bis(bromomethyl)-1,1'-binaphthyl with cyclic amines such as pyrrolidine, piperidine and 4-hydroxypiperidine. International Patent Publication No. WO 92/02505 to Castelijns also discloses use of a secondary amine in a catalytic transformation, i.e., in conversion of an unsaturated imine to a pyridine product, by reaction with an aldehyde or ketone.

The aforementioned organic catalysts are not, however, useful in catalyzing a broad range of chemical transformations, but are specific for a particular reaction and thus have limited utility. There is accordingly a need in the art for organic catalysts that are versatile with respect to the types of reactions that can be catalyzed, are inexpensive to synthesize, and are readily capable of scale-up for commercialization. It is also desirable that such catalysts be capable of preparing chiral products from starting materials that may be either chiral or achiral in nature.

SUMMARY OF THE INVENTION

Accordingly, it is a primary object of the invention to address the aforementioned need in the art and provide methods, catalyst compositions and reaction systems for chemically transforming a substrate, wherein the catalyst composition is nonmetallic, useful for catalyzing a wide variety of reactions and reaction types, relatively inexpensive to synthesize, and simple and straightforward to work with and scale up. Importantly, the catalyst composition may also contain a chiral non-racemic component that enables enantioselective catalysis and synthesis of a chiral nonracemic product.

It is another object of the invention to provide a process for transforming a compound containing a functional group to provide a product in which the functional group contains at least one newly formed covalent bond, wherein the transformation is carried out in the presence of a catalyst composition comprising an acid addition salt of an imidazolidinone.

It is yet another object of the invention to provide a chemical reaction wherein an nonmetallic, organic catalyst composition as provided herein lowers the LUMO (lowest unoccupied molecular orbital) of a substrate to facilitate reaction thereof.

It is a further object of the invention to provide such processes and reactions wherein the catalyst composition contains a chiral component.

It is still a further object of the invention to provide novel compounds, useful as catalyst compositions, in the form of acid addition salts of an imidazolidinone.

It is still an additional object of the invention to provide a reaction system composed of the aforementioned catalyst composition and a substrate such as an α,β-unsaturated carbonyl compound.

Additional objects, advantages and novel features of the invention will be set forth in part in the description which follows, and in part will become apparent to those skilled in the art upon examination of the following, or may be learned by practice of the invention.

In one aspect, then, the invention is directed to an imidazolidone salt having the structure of formulae (IV) or (IV-A)

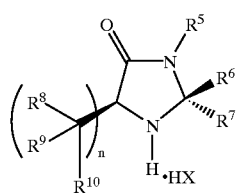

(IV)

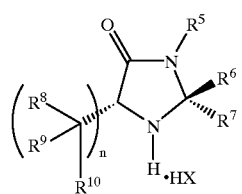

(IV-A)

wherein:

$R^5$, $R^6$ and $R^7$ are independently selected from the group consisting of hydroxyl, sulfhydryl, amino, substituted amino, carboxyl, hydrocarbyl (e.g., alkyl, alkenyl, alkynyl, aryl, alkaryl, alkaryl, etc.), substituted hydrocarbyl (e.g., substituted alkyl, alkenyl, alkynyl, aryl, alkaryl, alkaryl, etc.), heteroatom-containing hydrocarbyl (e.g., heteroatom-containing alkyl, alkenyl, alkynyl, aryl, alkaryl, alkaryl, etc.), and substituted heteroatom-containing hydrocarbyl (e.g., substituted heteroatom-containing alkyl, alkenyl, alkynyl, aryl, alkaryl, alkaryl, etc.);

the substituents $R^8$ and $R^9$ may be hydrido or halo, or they may be selected from the aforementioned substituent possibilities given for $R^5$, $R^6$ and $R^7$, and any two or more of $R^5$, $R^6$, $R^7$, $R^8$ and $R^9$ can be linked to form a cyclic group, typically through a hydrocarbylene, substituted hydrocarbylene, heteroatom-containing hydrocarbylene or substituted heteroatom- containing hydrocarbylene linkage;

the subscript "n" is 0 or 1;

the substituent $R^{10}$ is a cyclic group, either substituted or unsubstituted; and the Bronsted acid HX, which provides the anion $X^-$, may be selected from any number of substituted aromatic alcohols, organic acids, inorganic acids and combinations thereof, generally although not necessarily having a pKa of less than about 5.

In another aspect, the invention involves use of the aforementioned imidazolidinone salt as a catalyst composition. For example, compounds of formulae (IV) or (IV-A) can be used to catalyze the reaction of a first reactant containing a functional group having a π bond or an equivalent thereof (e.g., a δ bond having π bond-type reactivity, as in cyclopropyl moieties) with a second reactant. It is believed that by virtue of the interaction between the catalyst composition and the first reactant, the LUMO of the functional group of the first reactant is lowered relative to its initial state (i.e., prior to contact with the catalyst composition) and generally relative to the HOMO (highest occupied molecular orbital) of the second reactant as well. This LUMO-lowering in turn facilitates reaction of the functional group with the second reactant, enabling transformation of the first reactant by formation of new covalent bonds between the LUMO-lowered functional group and a second reactant (in either an intra- or intermolecular reaction). Suitable first reactants include, for example, α,β-unsaturated carbonyl compounds such as α,β-unsaturated ketones and α,β-unsaturated aldehydes.

In some embodiments, the salt maybe mixed with an excess of imidazolidinone to optimize catalytic activity or other aspects of the reaction that is being catalyzed.

As indicated in formulae (IV) and (IV-A), the imidazolidinone salt can be a chiral compound, i.e., the imidazolidinone component of the salt is chiral with respect to an axis, plane or center of asymmetry. Chiral imidazolidinones may be designed to provide high enantioselectivity, such that a desired enantiomer can be synthesized in enantiomerically pure form.

DETAILED DESCRIPTION OF THE INVENTION

Figure 1:
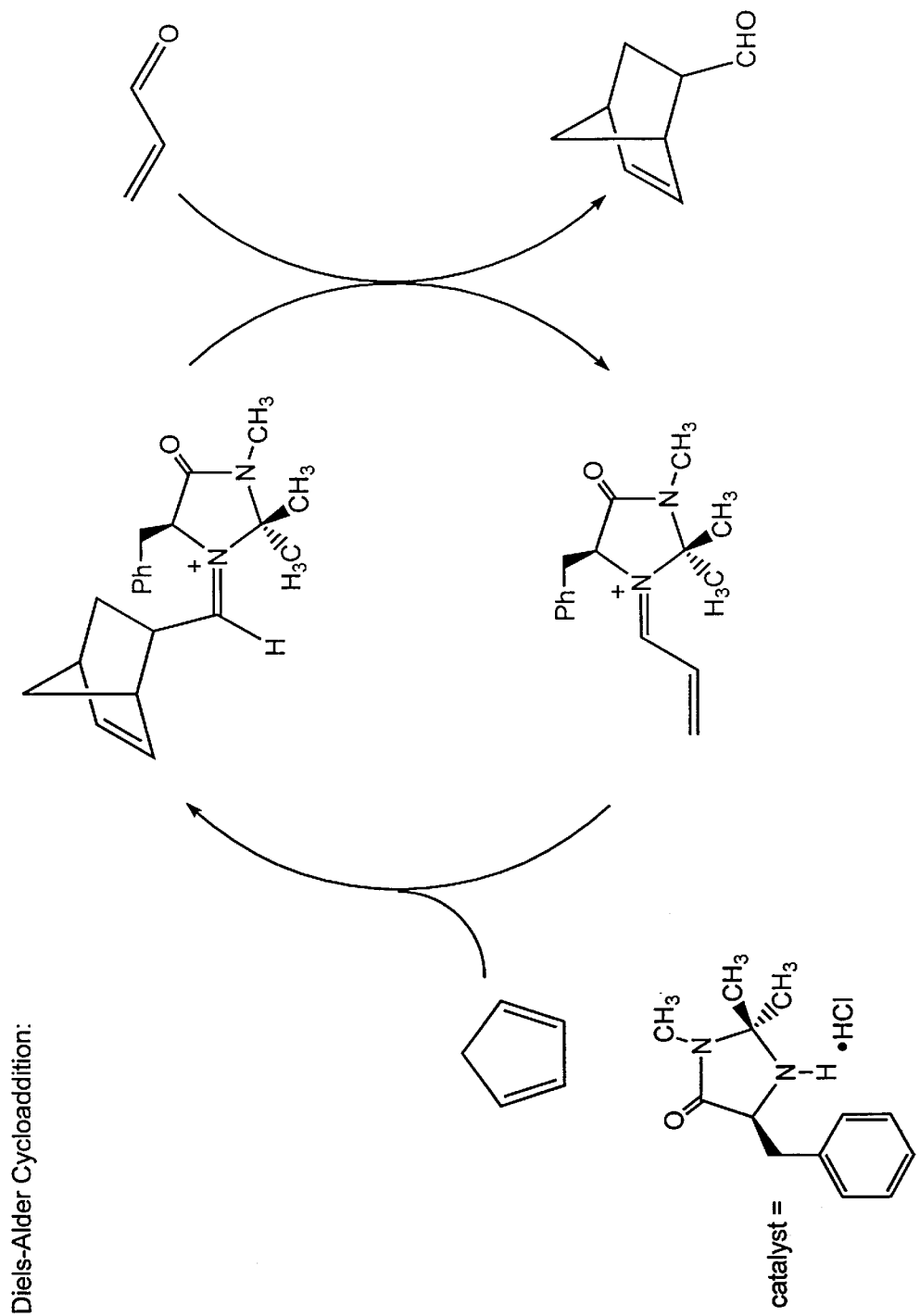
FIG. 1 schematically illustrates a Diels-Alder reaction catalyzed using a catalyst composition of the invention.

It is to be understood that unless otherwise indicated this invention is not limited to specific reactants, catalyst compositions, or synthetic methods. It is also to be understood that the terminology used herein is for the purpose of describing particular embodiments only, and is not intended to be limiting. For example, while the Diels-Alder reaction between a diene and dienophile is discussed throughout, the reaction is intended to be merely representative and not in any way limiting of the many types of reactions that can be catalyzed using the compositions and methods of the invention. As another example, while $\alpha,\beta$-unsaturated ketones and aldehydes are frequently used to exemplify suitable "first reactants," such compounds, again, are merely illustrative and not limiting of the reactants with which the present compositions and methods can be used.

As used in this specification and the appended claims, the singular forms "a," "an" and "the" include plural referents unless the context clearly dictates otherwise. Thus, reference to reference to "a reagent" includes mixtures of reagents, "a Bronsted acid" includes mixtures of Bronsted acids, "a catalyst composition" includes mixtures of catalyst compositions, "an imidazolidinone" includes mixtures of different imidazolidinones, and the like.

In describing and claiming the present invention, the following terminology will be used in accordance with the definitions set out below.

The following definitions pertain to chemical structures, molecular segments and substituents:

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl, s-propenyl, 2-propenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "aLkynyl" as used herein refers to a branched or unbranched hydrocarbon group typically although not necessarily containing 2 to about 24 carbon atoms and at least one triple bond, such as ethynyl, n-propynyl, n-butynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably 2, 3 or 4 carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as -O-alkyl where alkyl is as defined above. A "lower alkoxy" group intends an alkoxy group containing one to six, more preferably one to four, carbon atoms.

Similarly, the term "alkyl thio" as used herein intends an alkyl group bound through a single, terminal thioether linkage; that is, an "alkyl thio" group may be represented as -S-alkyl where alkyl is as defined above. A "lower alkyl thio" group intends an alkyl thio group containing one to six, more preferably one to four, carbon atoms.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," "halogenated aromatic" or "halogenated alkynyl") refers to an alkyl, alkenyl, aromatic or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

As used herein the term "silyl" refers to the -SiZ$^1$Z$^2$Z$^3$ radical, where each of Z$^1$, Z$^2$, and Z$^3$ is independently selected from the group consisting of hydrido and optionally substituted alkyl, alkenyl, alkynyl, aryl, aralkyl, alkaryl, heterocyclic, alkoxy, aryloxy and amino.

As used herein, the term "phosphino" refers to the group -PZ$^1$Z$^2$, where each of Z$^1$ and Z$^2$ is independently selected from the group consisting of hydrido and optionally substituted alkyl, alkenyl, alkynyl, aryl, aralkyl, alkaryl, heterocyclic and amino.

The term "amino" is used herein to refer to the group -NZ$^1$Z$^2$, where each of Z$^1$ and Z$^2$ is independently selected from the group consisting of hydrido and optionally substituted alkyl, alkenyl, alkynyl, aryl, aralkyl, alkaryl and heterocyclic.

The term "thio" is used herein to refer to the group -SZ$^1$, where Z$^1$ is selected from the group consisting of hydrido and optionally substituted alkyl, alkenyl, alkynyl, aryl, aralkyl, alkaryl and heterocyclic.

The terms "LUMO" and "HOMO" (abbreviations for lowest unoccupied molecular orbital and highest occupied molecular orbital, respectively) refer to the frontier orbitals of two reactants (such as a dienophile and diene, in a Diels-Alder reaction), with the LUMO referring to the vacant orbital of lowest energy, in a first reactant, and the HOMO referring to the orbital containing electrons of highest energy, in a second reactant. The present invention lowers the LUMO of a first reactant relative to its initial state, thereby facilitating reaction with a second reactant.

The term "chiral" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt.% of the composition in which it is contained, more preferably at least about 99 wt.% of that composition.

The term "enantioselective" refers to a chemical reaction that preferentially results in one enantiomer relative to a second enantiomer, i.e., gives rise to a product in which one enantiomer represents at least about 51 wt.% of the product. Preferably, in the enantioselective reactions herein, the selectively favored enantiomer represents at least about 85 wt.% of the product, optimally at least about 95 wt.% of the product.

The term "substrate" refers generally to a reactant, e.g., the "first reactant" herein or the "second reactant" herein.

As used herein all reference to the elements and groups of the Periodic Table of the Elements is to the version of the table published by the Handbook of Chemistry and Physics, CRC Press, 1995, which sets forth the new IUPAC system for numbering groups.

In one embodiment, then, the invention provides imidazolidinone salts for catalyzing a reaction, e.g., a reaction in which a compound containing a functional group is transformed to provide a product in which the functional group contains at least one newly formed covalent bond. The starting material that is transformed is generally represented by the structure of formula (I)

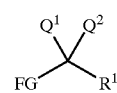

(I)

wherein FG comprises the functional group, R$^1$ is hydrido, hydrocarbyl, substituted hydrocarbyl, heteroatom-containing hydrocarbyl, substituted heteroatom-containing hydrocarbyl or silyl and is optionally covalently bound, directly or indirectly, to FG, and Q$^1$ and Q$^2$ are independently selected from the group consisting of $OR^1$, $SR^1$, $N(R^1)_2$, $NR^1(OR^1)$, $NR^1(SR^1)$, and $NR^1$—$N(R^1)_2$, or $Q^1$ and $Q^2$ together form =Q in which Q is O, S, $NR^1$, $N(OR^1)$, $N(SR^1)$ and N—$N(R^1)_2$. In some embodiments, it is preferred that =Q is other than =$NR^1$ or =$N(OR^1)$. The process involves reacting this first reactant with a second reactant in the presence of a catalyst composition comprising an acid addition salt of an imidazolidinone compound, as will be described in detail below.

In structural formula (I), FG, $Q^1$ and $Q^2$ are typically selected to enable formation of an intermediate in which the LUMO of the compound (particularly the LUMO of the fimctional group FG) is lowered relative to its initial state. LUMO lowering in this way in turn enables reaction such that new covalent bonds are formed between the LUMO-lowered functional group FG and a second reactant (in either an intra- or intermolecular reaction). While not wishing to be bound by theory, it is proposed that formation of the intermediate involves replacement of the C-$Q^1$ and C–$Q^2$ (or C=Q) bonds with a covalent bond of that carbon atom to a nitrogen atom in the imidazolidinone moiety in the catalyst composition. Preferred first reactants are wherein Ql and $Q^2$ together form a carbonyl moiety =O and wherein FG contains a π bond between two atoms that are α and β to the carbon atom bound to $Q^1$ and $Q^2$, e.g., FG may comprise A=B or A≡B wherein A is C or N, and B is N, C or 0. For example, FG may comprise C=C, C=C=C, C≡C, C=N, C≡N, C=O or C=S. In such a case, the first reactant may be represented by the structural formula (Ia)

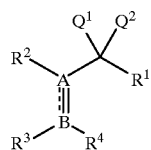

(Ia)

wherein A, B, $R^1$, $Q^1$ and $Q^2$ are as defined above, the dotted line represents an optional triple bond, and $R^2$, $R^3$ and $R^4$ are independently selected from the group consisting of hydrido, hydroxyl, sulfhydryl, amino, substituted amino, hydrocarbyl (e.g., alkyl, alkenyl, alkynyl, aryl, alkaryl, alkaryl, etc.), substituted hydrocarbyl (e.g., substituted alkyl, alkenyl, alkynyl, aryl, alkaryl, alkaryl, etc.), heteroatom-containing hydrocarbyl (e.g., heteroatom-containing alkyl, alkenyl, alkynyl, aryl, alkaryl, alkaryl, etc.), substituted heteroatom-containing hydrocarbyl (e.g., substituted heteroatom-containing alkyl, alkenyl, alkynyl, aryl, alkaryl, alkaryl, etc.), silyl and phosphino, or two or more of $R^1$, $R^2$, $R^3$ and $R^4$ are joined together in a ring structure, generally a five- or six-membered alicyclic group (e.g., $R^3$ and $R^4$ may together form a cyclohexyl ring). Alternatively FG may contain a functional equivalent of a π bond such as a cyclopropyl or substituted cyclopropyl group, i.e., a group that has π bond-type reactivity.

In a preferred embodiment, the first reactant is an α,β-unsaturated carbonyl compound, generally an α,β-unsaturated ketone or an α,β-unsaturated aldehyde, and may be represented by the structure of formula (II)

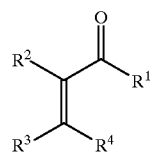

(II)

in which $R^1$, $R^2$, $R^3$ and $R^4$ are as defined above. As may be seen in formula (I)), the compound is an α,β-unsaturated ketone when $R^1$ is hydrocarbyl, substituted hydrocarbyl, heteroatom-containing hydrocarbyl or substituted heteroatom-containing hydrocarbyl, and an α,β-unsaturated aldehyde when $R^1$ is hydrido.

Examples of specific α,β-unsaturated carbonyl compounds having the structure of formula (I) thus include, but are not limited to, the following:

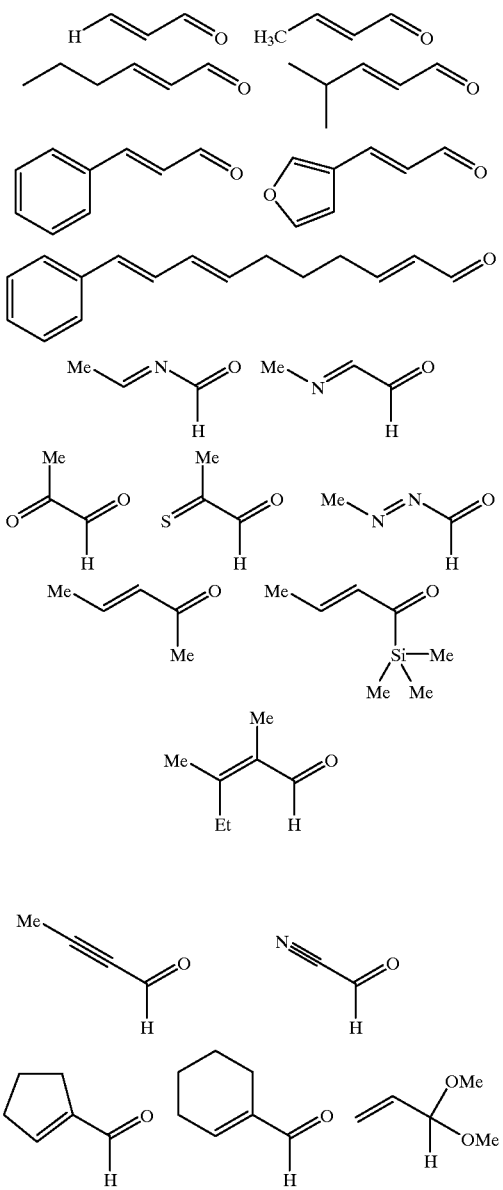

-continued

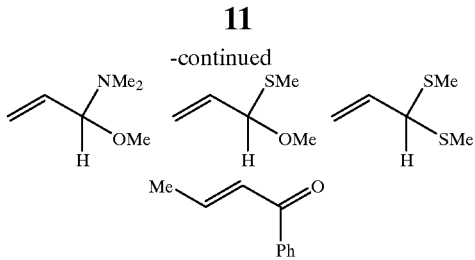

The catalyst composition, as noted earlier herein, comprises an acid addition salt of an imidazolidinone, wherein the imidazolidinone has the structure of formula (III)

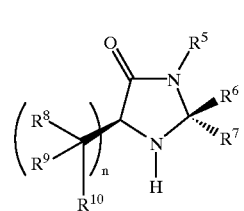
(III)

and the acid addition salt represents a Bronsted acid in ionic association with the imidazolidinone of structure (III), thus having the structure of formula (IV)

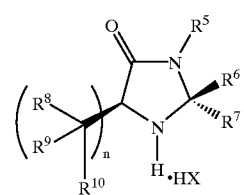
(IV)

In formulae (III) and (IV), $R^5$, $R^6$ and $R^7$ are independently selected from the group consisting of hydroxyl, sulfhydryl, amino, substituted amino, carboxyl, hydrocarbyl (e.g., alkyl, alkenyl, alkynyl, aryl, alkaryl, alkaryl, etc.), substituted hydrocarbyl (e.g., substituted alkyl, alkenyl, alkynyl, aryl, alkaryl, alkaryl, etc.), heteroatom-containing hydrocarbyl (e.g., heteroatom-containing alkyl, alkenyl, alkynyl, aryl, alkaryl, alkaryl, etc.), and substituted heteroatom-containing hydrocarbyl (e.g., substituted heteroatom-containing alkyl, alkenyl, alkynyl, aryl, alkaryl, alkaryl, etc.). Preferably, $R^5$, $R^6$ and $R^7$ are independently selected from the group consisting of hydroxyl, sulfhydryl, amino, substituted amino, carboxyl, alkyl, heteroalkyl, substituted alkyl, alkenyl, heteroalkenyl, substituted alkenyl, alkynyl, heteroalkynyl, substituted alkynyl, aryl, heteroaryl and substituted aryl. Most preferably, $R^5$, $R^6$ and $R^7$ are each lower alkyl, preferably methyl.

The substituents $R^8$ and $R^9$ may be independently hydrido or halo, or they may be selected from the aforementioned substituent possibilities given for $R^5$, $R^6$ and $R^7$. In a particularly preferred embodiment, $R^8$ and $R^9$ are hydrido. In addition, any two or more of $R^5$, $R^6$, $R^7$, $R^8$ and $R^9$ can be linked to form a cyclic group, typically through a hydrocarbylene, substituted hydrocarbylene, heteroatom-containing hydrocarbylene or substituted heteroatom- containing hydrocarbylene linkage.

The subscript "n" is 0 or 1, preferably 1.

The $R^{10}$ group is a cyclic moiety, and preferred $R^{10}$ groups are heterocyclic or aromatic. $R^{10}$ may or may not be substituted with the same or different substituents and suitable substituents are amino, halo, or any of the above-mentioned substituent possibilities given for $R^5$, $R^6$ and $R^7$. In a preferred embodiment, $R^{10}$ is an unsubstituted phenyl group.

The Bronsted acid HX (as shown in formula (IV)), which provides the anion $X^-$, is generally although not necessarily selected from acids having a pKa of less than about 5. Combinations of Bronsted acids may also be used. Suitable acids include both organic and inorganic acids, e.g., hydrochloric acid, hydrobromic acid, perchloric acid, sulfurous acid, sulfuric acid, sulfonic acids (including alkyl and aryl sulfonic acids), phosphoric acid, phosphonic acids (including alkyl and aryl phosphonic acids), nitric acid, nitrous acid, chromic acid, methylsulfonic acid, triflic acid, acetic acid, haloacetic acids, benzoic acid, propionic acid, fumaric acid, maleic acid, succinic acid, salicylic acid, mixtures thereof and the like. Particularly suitable are acids having structural formulas (V) or (VI)

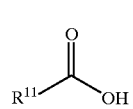
(V)

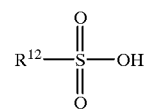
(VI)

wherein $R^{11}$ and $R^{12}$ are aryl, alkyl, substituted aryl or substituted alkyl. Preferred $R^{11}$ and $R^{12}$ groups are $-CR^{13}R^{14}R^{15}$ wherein $R^{13}$, $R^{14}$ and $R^{15}$ are independently hydrogen, halo or nitrite. Also preferred as Bronsted acids are substituted aromatic alcohols preferably having a pKa of less than about 5 and having the structural formula (VII)

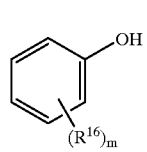
(VII)

wherein the $R^{16}$ substituents may be any electron-withdrawing substituents, and m is an integer from 1 to 5. Suitable $R^{16}$ substituents include, by way of example, nitro, cyano, sulfonate, halo (i.e., Cl, F, Br or 1) and halogenated alkyl (typically fluorinated alkyl, preferably perfluorinated lower alkyl such as trifluoromethyl). Anions (i.e., the $X^-$ moieties) can be in the form of polyanions derived from acid-containing solids or polymers. i.e. zeolites, resins, etc. It should also be noted that the anion $X^-$ of the Bronsted acid may or may not be chiral, and that those Bronsted acids that are chiral may be used in isomerically pure form or as a racemic mixture.

The imidazolidinone salt can be obtained commercially or synthesized using routine methodology known to those skilled in the art of synthetic organic chemistry and/or described in the pertinent texts and literature. The salt may be synthesized by admixing the imidazolidinone (in uncharged, free base form) with a Bronsted acid HX, at a desired molar ratio, generally in the range of approximately 1:100 to 100:1, typically about 1:10 to 10: 1, preferably about 1:2 to 2:1. Alternatively, the components of the salt, i.e., the uncharged imidazolidinone and the Bronsted acid, may be combined just prior to or during the catalyzed reaction. In still another embodiment, the uncharged imidazolidinone may be combined with at least one salt $M^{q+} \cdot qX^-$, thereby forming the desired imidazolidinone salt via ion exchange. A wide variety of salts may be used for this latter purpose, and the cation $M^{+q}$ can be virtually any cation, although q is generally 1, 2 or 3. Suitable M elements are typically chosen from Groups 2 to 13 of the Periodic Table of the Elements, but M may also be a polyatomic cation such as the ammonium ion $NH_4^+$. It should also be noted that the imidazolidinone salt can be prepared with two or more different Bronsted acids or metal salts, thereby forming a mixture of imidazolidinone salts, i.e., salts containing different anions $X^-$.

For purposes of exemplification, a detailed description of one method for synthesizing the imidazolidinone salt ((5S)-5-benzyl-2,2,3-trimethylimidazolidin-4-one hydrochloride) is described in Example 1.

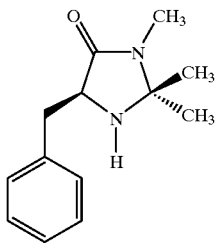

(5S)-5-BENZYL-2,2,3-TRIMETHYLIMIDAZOLIDIN-4-ONE HYDROCHLORIDE

It should be emphasized that imidazolidinone salts having the opposite enantiomeric configuration from that shown in formulae (III) and (IV) are possible, and also useful as catalytic compositions herein. Such structures are given by formulae (III-A) and (IV-A), below:

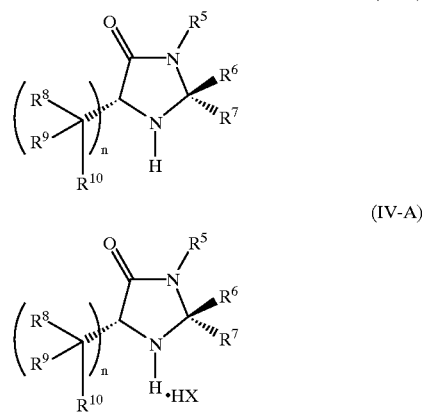

The second reactant may be any compound that is capable of reacting with the first reactant by virtue of the lowered LUMO of the first reactant in the presence of the catalyst composition. The second reactant may or may not be covalently linked, directly or indirectly, to the first reactant, i.e., the reaction between the first and second reactants may be either intramolecular or intermolecular. Selection of the second reactant will depend on the reaction of interest; thus, for example, in a Diels-Alder reaction, the second reactant is a diene (while the first reactant is a dienophile such as an α,β-unsaturated carbonyl compound). Examples of various reactants and corresponding reaction types are discussed in further detail below.

The imidazolidinone salt may also be combined with excess imidazolidinone to tune the reaction, i.e., improving catalytic activity, conversion or selectivity. The molar ratio of the imidazolidinone to the anion $X^-$ can be as high as about 100:1, although typically not exceeding about 20:1, and most typically not exceeding about 2:1.

In a preferred embodiment, the invention particularly provides a process for transforming an α,β-unsaturated carbonyl compound by reaction with a second reactant in the presence of a catalyst composition comprising an acid addition salt of an imidazolidinone having the structure of formula (IV) or (IV-A), wherein the α,β-unsaturated carbonyl compound has the structure of formula (II)

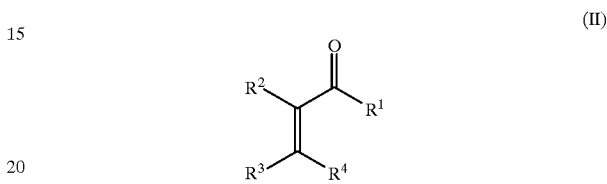

wherein $R^1$, $R^2$, $R^3$ and $R^4$ are as defined earlier herein.

Although other methods for lowering the LUMO of α,β-unsaturated carbonyl compounds have been proposed, for example using Lewis acid catalysis, Bronsted acid catalysis and in situ generated dienophiles (see, e.g., International Patent Publication WO 92/02505, cited supra, Yamaguchi et al. (1997) Tetrahedron 53 (32):11223–11236 and Yamaguchi et al. (1994) Tetrahedron Let. 35 (44):8233–8236), the present process has not been disclosed previously. Relative to prior methods, the present invention is useful in conjunction with a wide variety of reactions, in turn enabling preparation of a host of reaction products.

The catalytic compositions are the invention are useful, for example, in catalyzing cycloaddition reactions, 1,4-nucleophile conjugate addition reactions, 1,4 radical addition reactions, organometallic insertion reactions (including Heck reactions), ene reactions, and any combination thereof (including reactions occurring in tandem or cascade).

Figure 2:
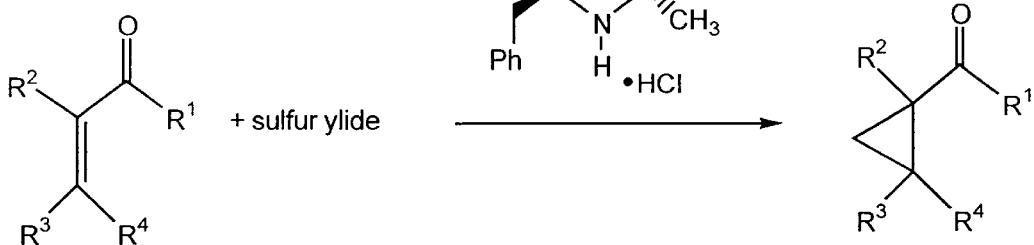
FIG. 2 schematically illustrates a cyclopropanation reaction catalyzed using a catalyst composition of the invention.
Figure 3:
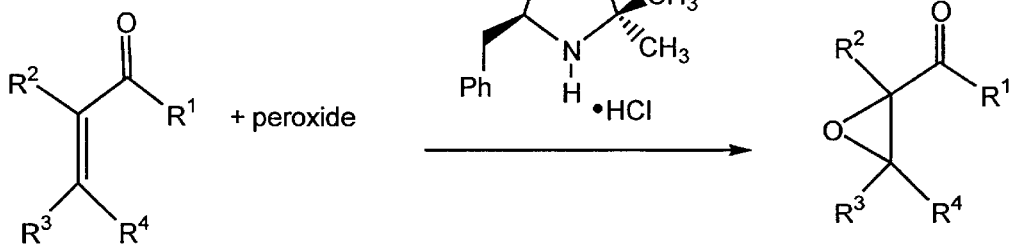
FIG. 3 schematically illustrates an epoxidation reaction catalyzed using a catalyst composition of the invention.
Figure 4:
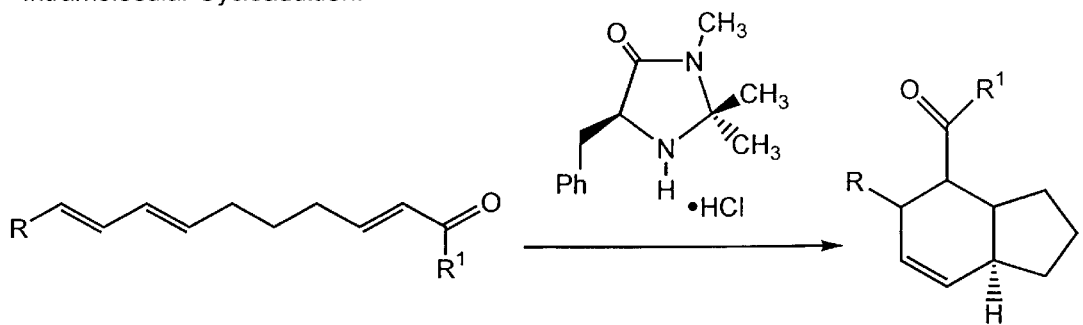
FIG. 4 schematically illustrates an intramolecular [4+2] cycloaddition reaction catalyzed using a catalyst composition of the invention.
Figure 5:
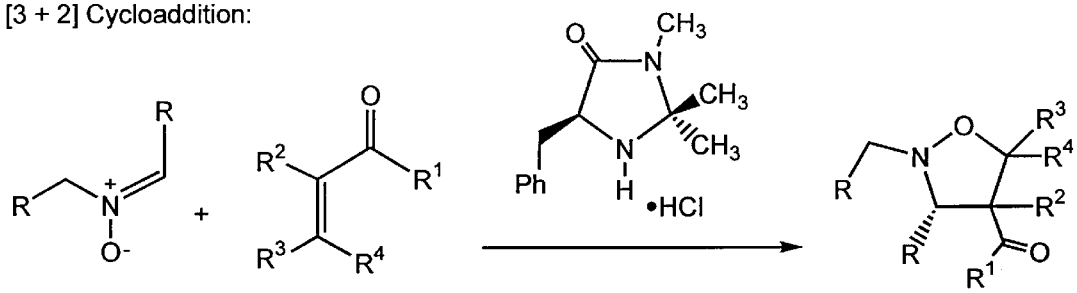
FIG. 5 schematically illustrates a [3+2] cycloaddition reaction catalyzed using a catalyst composition of the invention.
Figure 6:
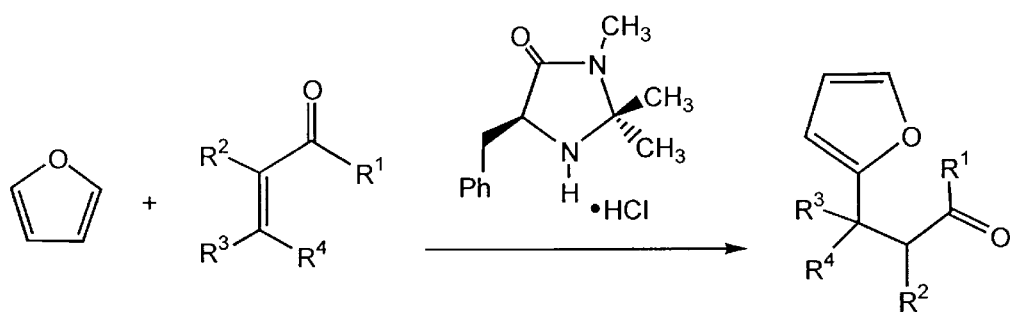
FIG. 6 schematically illustrates 1,4-conjugate addition of furan catalyzed using a catalyst composition of the invention.
Figure 7:
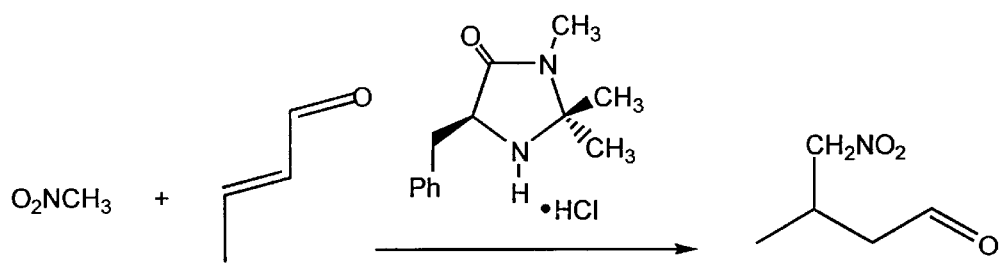
FIG. 7 schematically illustrates 1,4-conjugate addition of nitromethane catalyzed using a catalyst composition of the invention.

Cycloaddition reactions include, for example, [2+2] cycloaddition, [3+2] cycloaddition and [4+2] cycloaddition, with the latter reactions exemplified by Diels-Alder reactions, inverse demand Diels-Alder reactions, and hetero Diels-Alder reactions. An example of a Diels-Alder reaction catalyzed using a catalyst composition of the invention is illustrated in FIG. 1, wherein the first and second reactants are acrolein and cyclopentadiene, respectively. An intramolecular [4+2] cycloaddition reaction of the invention is illustrated in FIG. 4. A [3+2] cycloaddition reaction is illustrated in FIG. 5. Other types of cycloaddition reactions that can be catalyzed using the compositions and methods of the invention are described, for example, by Gothelf et al. (1998) Chem. Rev. 98:863–909. 1,4 Nucleophile conjugate addition reactions, include 1,4 carbon addition (e.g., cyclopropanation), 1,4 amine addition (e.g., aziridination), 1,4 oxygen addition (e.g., epoxidation), 1,4 sulfur addition, 1,4 hydride addition, and 1,4 organometallic addition. A cyclopropanation reaction of the invention is illustrated in FIG. 2, while an epoxidation reaction of the invention is illustrated in FIG. 3. Such reactions are examples of Michael additions, wherein the first reactant is an α,β-unsaturated carbonyl compound (or an alternative compound encompassed by structural formula (I) and the second reactant is a nucleophile containing a π bond, a lone pair bearing heteroatom, or a negative charge, as illustrated in FIGS. 6 and 7 (Michael addition of furan and nitromethane, respectively).

The foregoing list of possible reactions is intended to be illustrative and not in any way limiting of the reactions with which the present catalyst compositions and methods are useful. That is, the imidazolidinone salts of the invention are useful to catalyze a host of reactions and reaction types, of which those disclosed herein are merely representative.

Figure 8:
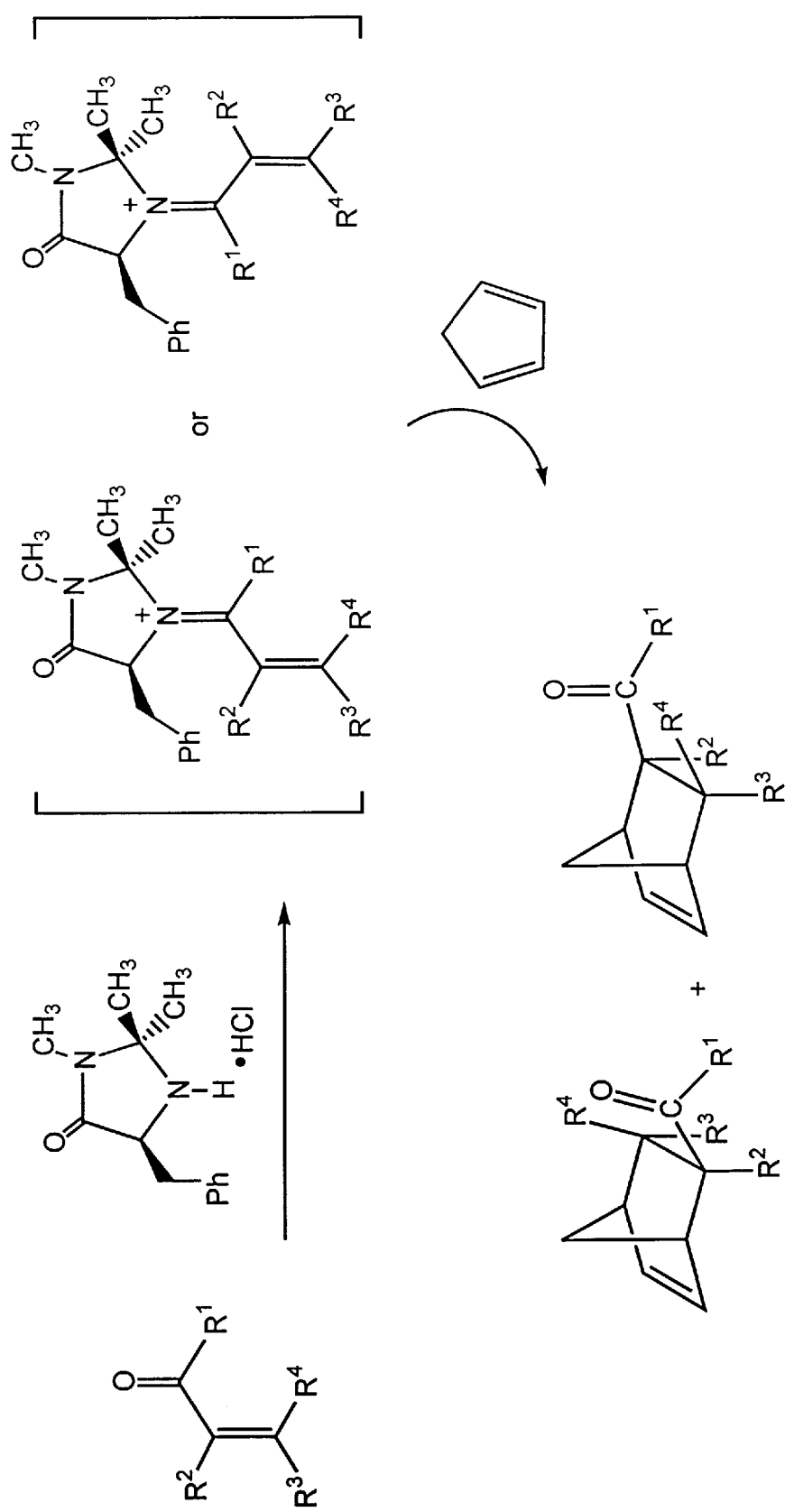
FIG. 8 schematically illustrates a Diels-Alder reaction between cyclopentadiene and an α,β-unsaturated carbonyl compound, wherein two possible enantiomeric products can result.
Figure 9:
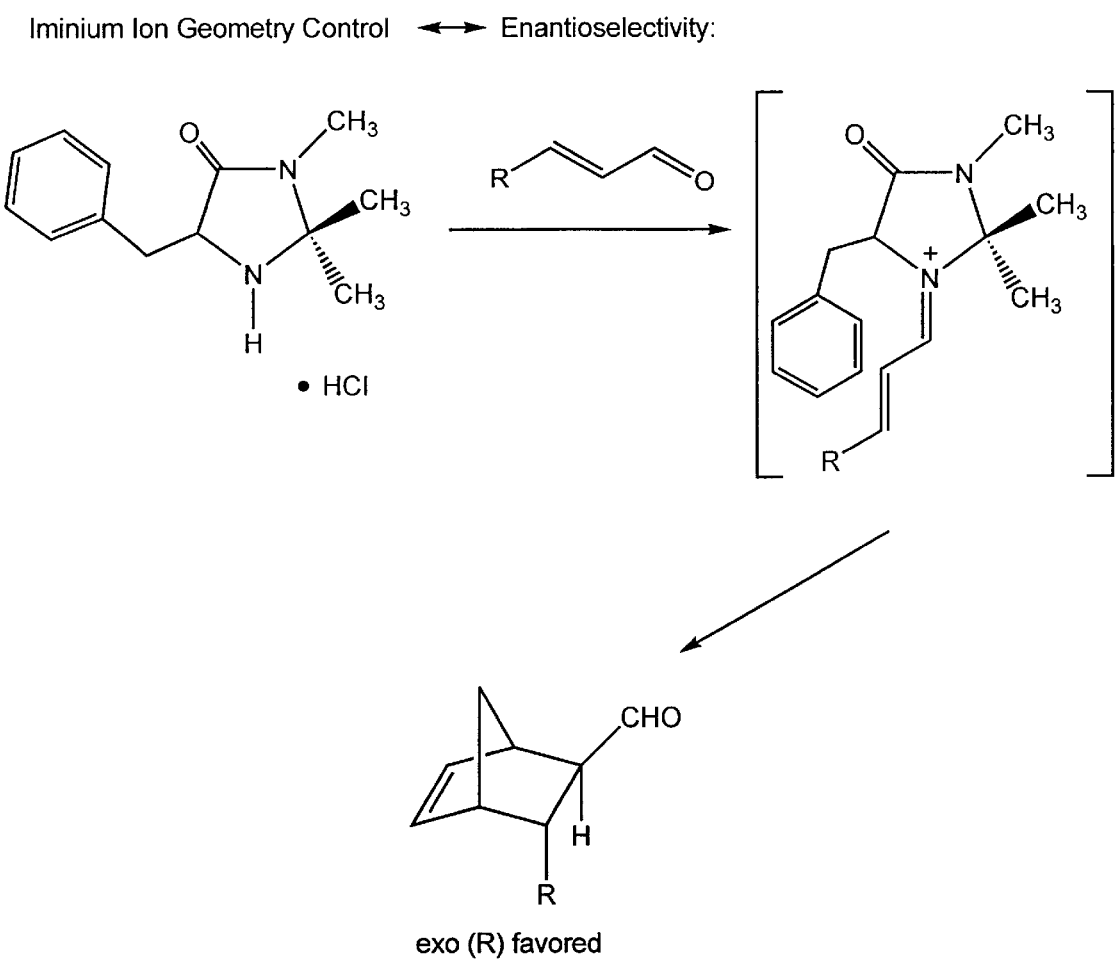
FIG. 9 schematically illustrates a reaction catalyzed using a chiral imidazolidinone salt, wherein enantioselectivity of the process can be controlled.

In another embodiment, the invention is directed to the production of chiral molecules from starting materials that may or may not be chiral themselves, using a compound of structural formula (I) as a substrate or "first reactant" (e.g., an α,β-unsaturated carbonyl compound) and a catalyst composition containing the chiral imidazolidinone salt of formulae (IV) or (IV-A). The imidazolidinone salt is substituted with a bulky substituent (i.e., a substituted or unsubstituted phenyl ring) so as to limit access to the activated double bond in the substrate (e.g., the α,β-unsaturated carbonyl compound) and thus provide enantiofacial discrimination. By way of example, the Diels-Alder reaction between cyclopentadiene and an α,β-unsaturated carbonyl compound can result in either of two iminium ion intermediates, leading to two possible enantiomeric products, as illustrated in FIG. 8. With an appropriately substituted imidazolidinone salt, as illustrated in FIG. 9, one can achieve control of the iminium ion geometry and thus the enantioselectivity of the process. Methods known to those skilled in the art, e.g., MM2 and MM3 techniques, may be advantageously employed to assist in the selection and substitution of the imidazolidinone salt to achieve the desired enantioselectivity.

Any of the reactions herein, including both preparation and use of the imidazolidinone salt, can be carried out on a solid support, using solid phase synthesis techniques. Solid-phase synthesis enables synthesis and use of the imidazolidinone salt in combinatorial chemistry processes, wherein an array or "matrix" of reactions are conducted in parallel on a single substrate. In such a case, the imidazolidinone itself (or the anion $X^-$) can be bound either directly or indirectly to the surface of a solid substrate, if indirectly, through a cleavable or noncleavable linker. For example, the imidazolidinone can be linked to the surface of a substrate through any of $R^5$ through $R^{10}$. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

Figure 10:
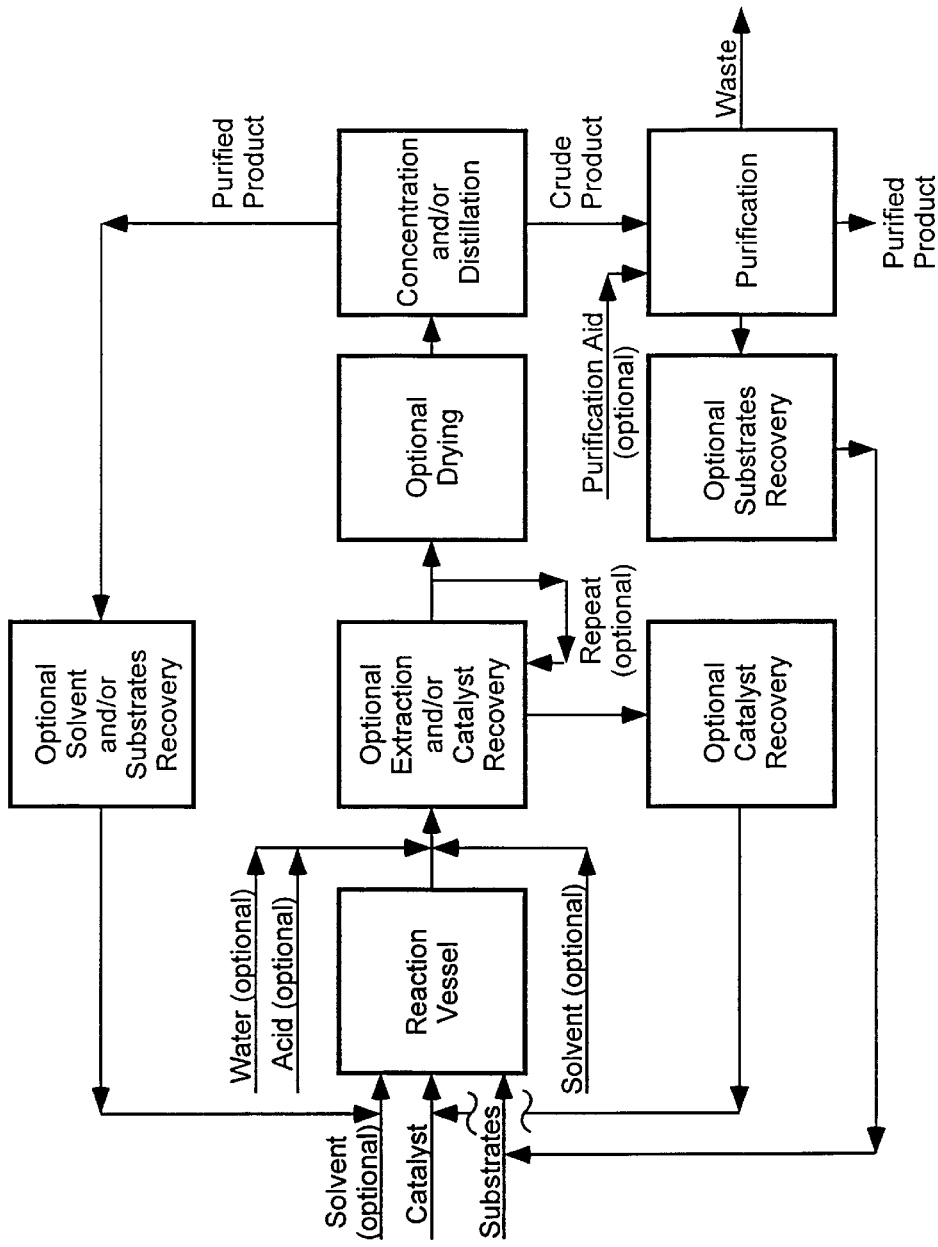
FIG. 10 is a flow chart illustrating a manufacturing method that may be used to implement the catalytic reactions of the invention.

Process conditions: The catalytic reactions of the invention are preferably although not necessarily carried out in water, organic solvents or ionic liquids, i.e., in any solvent that allows retention and regeneration of the catalyst composition and removal of the reaction product following completion of the reaction. The reactions may be carried out in batch, semi-continuously or continuously, in air or an inert atmosphere, at autogenous pressure or higher, depending, for example, on the nature of the catalyst composition and reactants used. The reaction temperature will generally be in the range of about −110° C. to 200° C., preferably in the range of about −50° C. to 100° C., most preferably in the range of about 0° C. to 50° C. The amount of catalyst composition is generally in the range of 1 mole % to 1 stoichiometric equivalent, and the ratio of the first reactant to the second reactant (for Diels-Alder reactions, the ratio of the enone to the diene) is generally in the range of about 100:1 to 1:100, preferably in the range of about 10:1 to 1:10. Industrially, the reaction may be scaled up to 10,000 gallons or more. Catalysis may be heterogeneous or homogeneous. It will be appreciated by those skilled in the art of catalysis that the aforementioned process conditions may vary depending on the particular reaction, the desired product, the equipment used, and the like. FIG. 10 illustrates, in detail, one possible manufacturing process. As shown in FIG. 10, the purified product is obtained after completion of the reaction, wherein an optional extraction and/or catalyst recovery step and/or drying is followed by concentration or distillation to give the crude product and purification, e.g., by chromatography, sublimation, precipitation, extraction, crystallization with optional seeding and/or co-crystallization aids.

The present invention thus represents an important contribution to the field of catalysis by providing an entirely new method of catalyzing chemical reactions using nonmetallic, organic catalyst compositions. The present processes and compositions are useful in conjunction with an enormous variety of reactants and reaction types, and, importantly, can be used to prepare chiral compounds in enantiomerically pure form, from either chiral or achiral starting materials.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

Experimental

In the following example, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

All solvents were used as obtained from commercial suppliers unless otherwise indicated. Other commercial reagents were purified prior to use following the guidelines of Perrin and Armarego, *Purification of Laboratory Chemicals,* Fourth Edition (Oxford, Butterworth-Heinemann, 1996). Thin-layer chromatography (TLC) was performed on EM Reagents 0.25 mm silica gel 60-F plates. Visualization of the developed chromatogram was performed by fluorescence quenching, $KMnO_4$ stain or p-anisaldehyde stain. Organic solutions were concentrated under reduced pressure on a Büichi rotary evaporator. Chromatographic purification of products was accomplished using forced-flow chromatography on ICN 60 32–64 mesh silica gel 63 according to the method of Still et al. (1978) *J. Org. Chem.* 43:2923.

$^1H$ and $^{13}C$ NMR spectra were recorded on Bruker DRX-500 (500 MHZ and 125 MHZ, respectively), AM-400 (400 MHZ and 100 MHZ), or AMX-300 (300 MHZ and 75 MHZ) instruments, as noted, and are internally referenced to residual protio solvent signals. Data for $^1H$ NMR are reported as follows: chemical shift (δ ppm), multiplicity (s=singlet, d=doublet, t=triplet, q=quartet, m=multiplet), coupling constant (Hz), integration, and assignment. Data for $^{13}$C are reported in terms of chemical shift. IR spectra were recorded on an ASI React-IR 1000 spectrometer and are reported in terms of frequency of absorption (cm$^{-1}$). Mass spectra were obtained from the University of California, Berkeley Mass Spectral facility. Spectral data was recorded using standard procedures. Gas chromatography was performed on Hewlett-Packard 5890A and 6890 Series gas chromatographs equipped with a split-mode capillary injection system and flame ionization detectors using the following columns: Bodman Chiraldex Γ-TA (30m×0.25 mm), Bodman Chiraldex β-PH (30m×0.25 mm), and C&C Column Technologies CC-1701 (30m×0.25 mm). HPLC analysis was performed on a Hewlett-Packard 1100 Series HPLC, UV detection monitored at 254 nm, using a Chiralcel OD-H column (25 cm) and a Chiralcel OD guard (5 cm).

Progress of the Diels-Alder reaction was typically monitored by TLC analysis, or in cases where necessary, by $^1$H NMR analysis of the reaction in situ in deuterated solvent or by GLC analysis of reaction aliquots.

Absolute configurations were determined by correlation to literature optical rotation values where indicated. Other absolute configurations were assigned by analogy.

General Procedure for Imidazolidinone Salt-Catalyzed Diels-Alder Reaction:

To a solution of (5S)-5-benzyl-2,2,3-trimethylimidazolidin-4-one hydrochloride (5) in CH$_3$OH/H$_2$O (95/5 v/v) was added the α,β-unsaturated aldehyde (1.0 M). The solution was stirred for 1–2 minutes before addition of the appropriate diene. Upon consumption of the limiting reagent, the reaction mixture was diluted with Et$_2$O and washed successively with H$_2$O and brine. The organic layer was dried (Na$_2$SO$_4$), filtered, and concentrated. Hydrolysis of the product dimethyl acetal was performed by stirring the crude product mixture in TFA:H$_2$O:CHCl$_3$ (1:1:2) for 2 hr at room temperature, followed by neutralization with saturated aqueous NaHCO$_3$. Purification of the Diels-Alder adduct was accomplished by silica gel chromatography.

EXAMPLE 1

Preparation of (5S)-5-benzyl-2,2,3-trimethylimidazolidin-4-one hydrochloride (5):

To a solution of ethanolic MeNH$_2$ (8.0 M, 60 mL) was added (S)-phenylalanine methyl ester hydrochloride (26.0 g, 121 mmol) and the resulting solution was stirred at room temperature until the amino ester was judged to be consumed as determined by TLC (20 hr). After removal of the organic solvents in vacuo, the residue was suspended in Et$_2$O and then concentrated. This Et$_2$O addition-removal cycle was repeated several times (to remove excess MeNH$_2$) until (S)-phenylalanine N-methyl amide hydrochloride was obtained as a white solid. This amide hydrochloride was then treated with saturated aqueous NaHCO$_3$ (100 mL) and the free amine was extracted with CHCl$_3$ (100 mL×3), dried (Na$_2$SO$_4$), filtered, and concentrated. To this residue was added MeOH (240 mL), acetone (45 mL, 605 mmol), and pTSA (230 mg, 1.2 mmol). The resulting solution was heated to reflux for 18 hr, cooled to room temperature, and then concentrated in vacuo. The residue was taken up in Et$_2$O, and a solution of HCl-dioxane (4.0 M) was added to precipitate compound (5). The precipitate was recrystallized from isopropanol to provide (5S)-5-benzyl-2,2,3-trimethylimidazolidin-4-one hydrochloride as colorless crystals in 59% overall yield from phenylalanine methyl ester hydrochloride (18.1 g, 71 mmol). IR (CH$_2$Cl$_2$) 3366, 1722, 1644, 1397 cm$^{-1}$; $^1$H NMR: (400 MHZ, d$_6$-DMSO) δ7.47–7.49 (d, J=7.2 Hz, 2H, PhH), 7.32–7.36 (m, 2H, PhH), 7.25–7.29 (m, 1H, PhH), 4.59–4.57 (br d, J=7.6 Hz, 1H, COCH), 3.35–3.42 (dd, J=15.0, 10.2 Hz, 1H, PhCHH), 3.22–3.26 (dd, J=15.0, 3.6 Hz, 1H, PhCHH), 2.76 (s, 3H, NCH$_3$), 1.70 (s, 3H, CHCH$_3$CH$_3$), 1.50 (s, 3H, CHCH$_3$CH$_3$); $^{13}$C NMR (100 MHZ, d$_6$-DMSO)δ166.9, 136.8, 129.7, 128.8, 127.2, 77.1, 57.7, 33.2, 25.2, 23.9, 22.2;HRMS (CI) exact mass calcd for C$_{13}$H$_{19}$N$_2$O requires m/z 219.1497, found m/z 219.1387. The enantiopurity was confirmed (>99% ee) by HPLC analysis of the free amine using a Chiracel OD-H column (6% isopropanol in hexanes, 1 mL/min); (S)-enantiomer t$_r$=14.1 min, (R)-enantiomer t$_r$=16.6 min.

EXAMPLE 2

Preparation of (1S, 2S, 3S, 4R)-3-Phenylbicyclo[2.2.1]hex-5-ene-2-carboxaldehyde and (1R, 2S, 3S, 4S)-3-Phenylbicyclo[2.2.1]hex-5-ene-2-carboxaldehyde (Table 1, entry 3):

Prepared according to the general procedure with (E)-cinnamaldehyde (6.36 mL, 50.4 mmol), cyclopentadiene (12.5 mL, 151 mmol), and 5 (640 mg, 2.5 mmol) to afford the title compound as a colorless oil in 99% yield (12.2 g, 50.0 mmol) after silica gel chromatography (10% EtOAc/hex); 1.0/1.3 endo:exo, endo 93% ee, exo 93% ee. Product ratios were determined by GLC (Bodman B-PH column, 60° C., 1.5° C./min gradient, 23 psi); endo isomers t$_r$=53.1 min, 53.4 min, exo isomers t$_r$=52.2 min, 52.7 min. $^1$H NMR, $^{13}$C NMR, and IR data were consistent with previously reported values (see Ishihara et al. (1998), supra).

EXAMPLE 3

Preparation of (1S, 2R, 3S, 4R)-3-Methylbicyclo[2.2.1]hex-5-ene-2-carboxaldehyde and (1R, 2R, 3S, 4S)-3-Methylbicyclo[2.2.]hex-5-ene-2-carboxaldehyde (Table 2, entry 1):

Prepared according to the general procedure with (E)-crotonaldehyde (871 μL, 10.0 mmol), cyclopentadiene (2.50 mL, 30.0 mmol), and 5 (109 mg, 0.50 mmol) to afford the title compound as a colorless oil in 75% yield (1.02 g, 7.5 mmol) after silica gel chromatography (3% EtOAc/hex); 1.0/1.0 endo:exo, endo 90% ee, exo 86% ee. Product ratios were determined by GLC (Bodman Γ-TA column, 50° C., 2° C./min gradient, 23 psi); (1S, 2R, 3S, 4R) endo isomer t$_r$=24.7 min, (1R, 2S, 3R, 4S) endo isomer t$_r$=25.0 min, exo isomers t$_r$=22.4 min, 22.9 min. $^1$H NMR, $^{13}$C NMR, and IR data for the endo isomer were consistent with previously reported values (see Ishihara et al. (1998) *J. Am. Chem. Soc.* 120:6920–6930). The endo isomer was reduced to the corresponding alcohol (4 equiv NaBH$_4$ in MeOH (0.1 M)) and purified by silica gel chromatography for correlation of optical rotation with the literature value: [α$_D$]$^{20}$ =+73.6 ⓒ=0.92, 95% EtOH). Literature [α$_D$]$^{20}$ =+86.6 ⓒ=1.2, 95% EtOH) (see Sartor et al. (1990) *Synlett*, pp. 197–198). Exo isomer: IR (CH$_2$Cl$_2$) 2968, 1714 cm$^{-1}$; $^1$H NMR (400 MHZ, CDCl$_3$) δ9.78–9.79 (d, J=2.8 Hz, 1H, CHO), 6.23–6.25 (dd, J=5.7, 3.1 Hz, 1H, CH=CH), 6.15–6.17 (dd, J=5.7, 3.0 Hz, 1H, CH=CH), 3.02 (br s, 1H, CHCH=CH), 2.79 (br s, 1H, CHCH=CH), 2.37–2.45 (m, 1H, CHCHO), 1.70–1.73 (m, 1H, CHCH$_3$), 1.44–1.48 (m, 2H, CHH), 0.89–0.91 (d, J=6.9 Hz, CHCH$_3$); $^{13}$C NMR (100 MHZ, CDCl$_3$)δ203.8, 136.3, 135.9, 60.0, 47.5, 47.4, 45.3, 35.7, 18.8; HRMS (EI) exact mass calcd for (C$_9$H$_{12}$O) requires m/z 136.0888, found m/z 136.0892; [α$_D$]$^{20}$=+91(c=0.81, CHCl$_3$).

EXAMPLE 4

Preparation of (1S, 2R, 3S, 4R)-3-Propyl-bicyclo[2.2.]hept-5-ene-2-carboxaldehyde and (1R, 2R, 3S, 4S)-3-Propyl-bicyclo[2.2.1]hept-5-ene-2-carboxaldehyde (Table 2, entry 2):

Prepared according to the general procedure with (E)-hex-2-enal (142 μL, 1.22 mmol), cyclopentadiene (302 μL, 3.66 mmol), and 5 (16 mg, 0.061 mmol) to provide the title compound as a colorless oil in 92% yield (184 mg, 1.12 mmol) after silica gel chromatography (10% EtOAc/hex); 1.0:1.0 endo:exo; endo 90% ee; exo 86% ee. Product ratios were determined by GLC (Bodman Γ-TA column, 100° C. isotherm, 23 psi); exo isomers $t_r$=25.6 min and 26.7 min, endo isomers $t_r$=30.2 min and 30.9 min. $^1$H NMR, $^{13}$C NAMR and IR data for the endo isomer were consistent with previously reported values (Ishiara et al. (1998), supra). Exo isomer: IR (CH$_2$Cl$_2$)1719, 1466, 1456 cm$^{-1}$; $^1$H NMR (400 MHZ, CDCl$_3$)δ9.76 (d, J=2.7 Hz, 1 H, CHO), 6.19 (dd, J=5.6, 3.2 Hz, 1H, CH=CH), 6.11 (dd, J=5.6, 2.9 Hz, 1H, CH=CH), 3.00 (br s, 1H, CHCH=CH), 2.85 (br s, 1H, CHCH=CH), 2.23–2.30 (m, 1H, CHCH$_2$CH$_2$), 1.72–1.76 (m, 1H, CHCHO), 1.00–1.47 (m, 6H, CHCH$_2$CH, CH$_2$CH$_2$CH$_3$), 0.86 (t, J=7.2 Hz, 3H, CH$_2$CH$_3$); $^{13}$C NMR (100 MHZ, CDCl$_3$)δ203.9, 136.0, 135.9, 58.7, 47.0, 45.7, 44.8, 41.6, 36.4, 21.6, 14. 1; HRMS (EI) exact mass calcd for (C$_{11}$H$_{16}$O) requires m/z 164.1201, found m/z 164.1200; $[α]_D$=+89.4 ©=2.7, CHCl$_3$).

EXAMPLE 5

Preparation of (1S, 2S, 3S, 4R)-3-Isopropyl-bicyclo[2.2.1]hept-5-ene-2-carboxaldehyde and (1R, 2S, 3S, 4S)-3-Isopropyl-bicyclo[2.2.1]hept-5-ene-2-carboxaldehyde (Table 2, entry 3):

Prepared according to the general procedure with (E)-4-methyl-pent-2-enal (142 μL, 1.22 mmol), cyclopentadiene (302 μL, 3.66 mmol), and 5 (16 mg, 0.061 mmol) to afford the title compound as a colorless oil in 81% yield (162 mg, 0.99 mmol) after silica gel chromatography (10% EtOAc/hex); 1.0:1.3 endo:exo; endo 93% ee; exo 84% ee. Product ratios were determined by GLC (Bodman Γ-TA column, 100° C. isotherm, 23 psi); endo isomers $t_r$=29.7 min and 30.5 min, exo isomers $t_r$=25.5 min and 27.2 min. Endo isomer: IR (CH$_2$Cl$_2$) 1719, 1469, 1387, 1368, 1333 cm$^{-1}$; $^1$H NMR (400 MHZ, CDCl$_3$)δ9.36 (d, J=3.4 Hz, 1H, CHO), 6.26 (dd, J=5.7, 3.2 Hz, 1H, CH=CH), 6.06 (dd, J=5.7, 2.8 Hz, 1H, CH=CH), 3.11 (m, 1H, CHCH=CH), 2.85 (m, 1H, CHCH=CH), 2.49 (m, 1H, CHCHO), 1.41–1.52 (m, 3H, CHCH(CH$_3$)$_2$, CHCH$_2$CH), 1.29–1.35 (m, 1H, CH(CH$_3$)$_2$), 1.01 (d, J=6.5 Hz, 3H, CH(CH$_3$)$_2$), 0.91 (d, J=6.6 Hz, 3H, CH(CH$_3$)$_2$); $^{13}$C NMR (100 MHZ, CDCl$_3$)δ205.2, 138.9, 133.0, 58.6, 50.0, 46.5, 45.2, 45.1, 32.8, 21.9, 21.8; HRMS (EI) exact mass calcd for (C$_{11}$H$_{16}$O) requires m/z 164.1201, found m/z 164.1198; $[α]_D$=+44©=0.47, CHCl$_3$). Exo isomer: IR (CH$_2$Cl$_2$) 1719, 1465, 1368, 1336 cm$^{-1}$; $^1$H NMR (400 MHZ, CDCl$_3$)δ9.78 (d, J=2.6 Hz, 1H, CHO), 6.19 (dd, J=5.6, 3.1 Hz, 1H, CH=CH), 6.15 (dd, J=5.6, 2.8 Hz, 1H, CH=CH), 3.02 (br s, 1H, CHCH=CH), 2.96 (br s, 1H, CHCH=CH), 1.84–1.92 (m, 2H, CHCHO, CHC(H)HCH), 1.38–1.47 (m, 2H, CHCH(CH$_3$)$_2$, CHC(H)HCH), 0.97–1.08 (m, 1H, CH(CH$_3$)$_2$), 0.94 (d, J=6.2 Hz, 3H, CH(CH$_3$)$_2$), 0.84 (d, J=6.4 Hz, 3H, CH(CH$_3$)$_2$); $^{13}$C NMR (100 MHZ, CDCl$_3$) δ204.1, 136.2, 135.7, 57.9, 50.2, 46.9, 45.0, 44.9, 32.4, 22.0, 21.5; HRMS (EI) exact mass calcd for (C$_{11}$H$_{16}$O) requires m/z 164.1201, found m/z 164.1202; $[α]_D$=+82.8 ©=1.7, CHCl$_3$).

EXAMPLE 6

Preparation of (1S, 2S, 3S, 4R)-3-Furan-2-yl-bicyclo[2.2.1]hept-5-ene-2-carboxaldehyde and (1R, 2S, 3S, 4S)-3-Furan-2-yl-bicyclo[2.2.1]hept-5-ene-2-carboxaldehyde (Table 2, entry 5):

Prepared according to the general procedure with (E)-3-furyl-acrolein (166 mg, 1.36 mmol), cyclopentadiene (329 μL, 3.99 mmol) and 5 (34 mg, 0.13 mmol) to afford the title compound as a colorless oil as a mixture of acetal and aldehyde in 88% yield (5.7:1, 270 mg) after silica gel chromatography (10% EtOAc/hex); 1.1:1.0 endo:exo; endo 93% ee; exo 91% ee. A small sample of the aldehyde was purified by HPLC for characterization purposes. Product ratios were determined by GLC (Bodman Γ-TA column, 70° C., 5° C./min gradient, 23 psi); exo isomers $t_r$=17.4 min and 17.7 min, endo isomers $t_r$=17.9 min and 18.1 min. Endo isomer: IR (CH$_2$Cl$_2$) 1718, 1506, 1332cm$^{-1}$; $^1$H NMR (500 MHZ, CDCl$_3$)δ9.56 (d, J=1.9 Hz, 1H, CHO), 7.32 (d, J=1.0 Hz, 1H, furyl), 6.35 (dd, J=5.6, 3.1 Hz, 1H, CH=CH), 6.30 (dd, J=3.1, 1.9 Hz, 1H, furyl), 6.13 (dd, J=5.6, 2.7 Hz, 1H, CH=CH), 6.07 (d, J=3.2 Hz, 1H, furyl), 3.33 (br s, 1H), 3.13–3.09 (m, 1H), 3.08–3.04 (m, 2H), 1.78 (br d, J=8.7, 1H), 1.59–1.53 (m, 2H); $^{13}$C NMR (125 MHZ, CDCl$_3$) δ202.5, 157.0, 141.3, 138.1, 133.7, 110.1, 105.0, 58.3, 48.5, 47.4, 44.6, 39.7; HRMS exact mass calcd for (C$_{12}$H$_{12}$O) requires m/z 188.0837, found m/z 188.0842; $[α]_D$=+157©= 0.28, CHCl$_3$). Exo isomer: IR (CH$_2$Cl$_2$) 1717, 1506, 1334 cm$^{-1}$; $^1$H NMR (500MHZ, CDCl$_3$)δ9.90 (d, J=1.7Hz, 1H, CHO), 6.29 (dd, J=5.6, 3.2Hz, 1H, CH=CH), 6.23 (dd, J=3.1, 1.9 Hz, 1H, furyl), 6.05 (dd, J=5.6,2.9 Hz, 1H, CH=CH), 5.89 (d, J=3.2, 1H, furyl), 3.70 (t, J=4.3 Hz, 1H), 3.26 (br s, 1H, CHCH=CH), 3.20 (br s, 1H, CHCH=CH), 2.50 (d, J=5.1 Hz, 1H, CHCHO), 1.57 (br s, 1H), 1.55–1.48 (m, 2H); $^{13}$C NMR (125 MHZ, CDCl$_3$)δ201.9, 156.9, 141.1, 136.6, 136.2, 110.0, 105.0, 58.2, 46.9, 46.9, 44.9, 39.1; HRMS exact mass calcd for (C$_{12}$H$_{12}$O$_2$) requires m/z 188.0837, found m/z 188.0838; $[α]_D$=+210 ©=0.53, CHCl$_3$).

EXAMPLE 7

Preparation of (1S, 8R, 9S, 10S)-1,8-Diphenyl-10-methyl-11-oxa-tricyclo[6.2.1.0$^{2,7}$]undeca-2(7),3,5-triene-9-carboxaldehyde (Table 3, entry 1):

To a 10° C. solution of 5 (13 mg, 0.058 mmol), 1,3-diphenylisobenzofuran (162 mg, 0.60 mmol), and MeOH (12 μL, 0.30 mmol) in DMF/H$_2$O (95/5 v/v, 1.0 M) was added (E)-crotonaldehyde (25 μL, 0.30 mmol). The solution was stirred at 10° C. for 24 h. The reaction mixture was then diluted with Et$_2$O (10 mL) and washed with H$_2$O (10 mL). The aqueous layer was extracted with Et$_2$O (10 mL×2) and the combined organics were dried (Na$_2$SO$_4$), and concentrated. Purification by silica gel chromatography (7% EtOAc/hex) afforded the title compound as a yellow solid in 75% yield (76 mg, 0.22 mmol); 35:1 exo:endo; 96% ee. Product ratios were determined, after reduction to the corresponding alcohol (4 eq NaBH$_4$, EtOH (0.1 M)), by HPLC (Chiralcel OD-H column, 3% EtOAc/hex, 1.0 mL/min) exo isomers $t_r$=14.1 min and 15.3 min, endo isomers $t_r$=16.5 min and 20.8. IR (CH$_2$Cl$_2$) 3066, 3041, 2828, 2729, 1722, 1603, 1499, 1457, 1448, 1381, 1355, 1309 cm$^{-1}$; $^1$H NMR (500 MHZ, CDCl$_3$)δ9.36 (d, J=5.8 Hz, 1H, CHO), 7.73–7.78 (m, 2H,ArH), 7.43–7.57 (m, 7H,ArH), 7.35–7.40 (m, 1H,ArH), 7.16–7.26 (m, 3H, ArH), 7.04–7.08 (m, 1H, ArH), 3.08 (dq, J=6.9,4.1 Hz, 1H, CHCH$_3$), 2.56 (dd, J =5.8, 4.2 Hz, 1H, CHCHO), 0.96 (d, J=6.9 Hz, 3H, CH$_3$); $^{13}$C NMR (125

MHZ)δ201.9, 147.4, 145.0, 145.0, 136.6, 135.7, 135.5, 128.8, 128.6, 128.0, 127.4, 127.3, 127.0, 126.0, 125.5, 121.7, 118.5, 91.4, 89.2, 66.0, 43.0, 34.2, 30.3, 16.5; HRMS exact mass calcd for ($C_{24}H_{20}O_2$) requires m/z 341.1541, found m/z 341.1542; $[\alpha]_D$=−82.4 ©=1.0, $CHCl_3$).

EXAMPLE 8

Preparation of (2R)-Bicyclo[2.2.2]oct-5-ene-2-carboxaldehyde (Table 3, entry 2):

To a solution of 5 (32 mg, 0.12 mmol) in $CH_3CN/H_2O$ (95/5 v/v, 1.0 M) was added acrolein (501 μL, 7.5 mmol), and cyclohexadiene (238 μL, 2.5 mmol). The solution was stirred for 24 h, after which time the reaction mixture was diluted with $Et_2O$ (10 mL) and washed with $H_2O$ (10 mL). The aqueous layer was extracted with $Et_2O$ (10 mL×2) and the combined organics were dried ($Na_2SO_4$), and concentrated. Purification by silica gel chromatography (10% ether/pentane) afforded the title compound as a colorless oil in 82% yield (280 mg, 2.06 mmol); 14:1 endo:exo; 94% ee. Product ratios were determined by GLC (Bodman Γ-TA column, 75° C. isotherm, 23 psi) $t_r$=51.0 min and 54.4 min. $^1H$ NMR, $^{13}C$ NMR, and IR data were consistent with previously reported values (Ishihara et al. (1998), supra).

EXAMPLE 9

Preparation of (1R)-4-methyl-3-cyclohexene-1-carboxaldehyde (Table 3, entry 3):

To a 0° C. solution of 5 (32 mg, 0.12 mmol) in $CH_3NO_2/H_2O$ (95/5 v/v, 1.0 M) was added acrolein (1.0 mL, 15 mmol), and isoprene (0.50 mL, 5 mmol). The solution was stirred at 0° C. for 7 hr, then directly placed onto a silica gel column and eluted with 3% $Et_2O$/pentane, affording the title compound as a colorless oil in 84% yield (745 mg, 89% ee). Product ratios were determined by GLC (Bodman Γ-TA column, 35° C., 0.25° C./min gradient, 23 psi) $t_r$=84.1 min, 85.3 min. $^1H$ NMR, $^{13}C$ NMR, and IR data were consistent with previously reported values (see Ishihara et al. (1998), supra). The absolute configuration was determined by oxidation to 4-methyl-3-cyclohexene-1-carboxylic acid and correlation of the optical rotation to the reported value; see Poll et al. (1985) Tetrahedron Lett. 26:3095–3098. To the aldehyde (255 mg, 2 mmol) was added a solution of isobutylene in THF (2.0 M, 30 mL) followed by tBuOH-$H_2O$ (5/1, 20 mL), KH2PO4 (840 mg, 6 mmol), and $NaClO_2$ (540 mg, 6 mmol). The heterogenous mixture was stirred for 4 hr, then partitioned between EtOAc and $H_2O$. The organic extract was washed with brine, dried ($MgSO_4$), and concentrated. The white solid was purified by silica gel chromatography (20% EtOAc/hex): $[\alpha]_D^{20}$=+89 ©=4.0, 95% EtOH). Literature $[\alpha]_D^{20}$=−107 ©=4, 95% EtOH) for (S)-4-methyl-3-cyclohexene-1-carboxylic acid.

EXAMPLE 10

Preparation of (1R)4-phenyl-3-cyclohexene-1-carboxaldehyde (Table 3, entry 4):

To a 0° C. solution of 2-phenyl-1,3-butadiene (89 mg, 0.68 mmol) in $CH_3NO_2/H_2O$ (95/5 v/v, 1.0 M) was added 5 (29.8 mg, 0.14 mmol) and acrolein (135 μL, 2.1 mmol). The solution was stirred at 0° C. for 7 hr, then directly placed onto a silica gel column and eluted with 5% EtOAc/hex affording the title compound as a coloeless oil in 90% yield (114 mg, 0.61 mmol, 83% ee). Product ratios were determined, after reduction to the corresponding alcohol (4 eq $NaBH_4$, MeOH (0.1 M)), by HPLC (Chiralcel OD-H column, 6% isopropanol in hexanes, 1 mL/min) $t_r$=16.2 and 20.4, min. (1R)-4-phenyl-3-cyclohexene-1-carboxaldehyde: IR ($CH_2Cl_2$) 2926, 2837, 2714, 1722, 1494, 1444 $cm^{-1}$; $^1H$ NMR (400 MHZ, $CDCl_3$)δ9.78 (s, 1H, CHO), 7.40–7.23 (m, 5H, ArH), 6.16–6.12 (m, lH, PhC=CH), 2.64–2.50 (m, 5H), 2.23–2.15 (m, 1H), 1.90–1.79 (m, 1H). $^{13}C$ NMR (100 MHZ, $CDCl_3$)δ204.2, 141.6, 136.8, 128.2, 126.9, 125.0, 122.0, 45.7, 26.0, 25.0, 22.6; HRMS (CI) exact mass calcd for ($C_{13}H_{19}N_2OCl$) requires m/z 186.1045, found m/z 186.1041. (1R)-4-phenyl-3-cyclohexene-1-ol: IR ($CH_2Cl_2$) 3374, 3289, 2918, 2860, 1444, 1034 $cm^{-1}$; $^1H$ NMR (500 MHZ, $CDCl_3$)δ7.41–7.39 (d, J=7.6 Hz, 2H, o-PhH), 7.34–7.31 (t, J=7.7 Hz, 2H, m-PhH), 7.26–7.22 (m, 1H,p-PhH), 6.13 (br, 1H, PhC=CH), 3.66–3.58 (m, 2H, $CH_2OH$), 2.58–2.41 (m, 2H), 2.40–2.31 (m, 1H), 2.05–1.83 (m, 3H), 1.72–1.68 (s, 1H), 1.50–1.41 (m, 1H); $^{13}C$ NMR (125 MHZ, $CDCl_3$)δ142.1, 136.5, 128,2, 126.6, 124.9, 123.3, 67.6, 35.9, 28.8, 26.8, 25.7; HRMS (CI) exact mass calcd for ($C_{13}H_{19}N_2OCl$) requires m/z 188.1201, found m/z 188.1203.

EXAMPLE 11

Preparation of (1R, 2S)-2,4-Dimethyl-cyclohex-3-ene-l-carboxaldehyde (Table 3, entry 5):

To a -10° C. solution of 5 (27 mg, 0.11 mmol) in $CH_3CN/H_2O$ (95/5 v/v) was added acrolein (102 μL, 1.53 mmol), and 2-methyl-1,3-pentadiene (60 μL, 0.51 mmol, 1.0 M). The solution was stirred for 31 h then filtered through a silica plug with $CH_2Cl_2$. To the eluent was added (R,R)-2,4-pentanediol (160 mg, 1.54 mmol) and a single crystal of pTSA. The solution was allowed to stand 10 h before concentration and purification by silica gel chromatography (10% EtOAc/hex) affording the (R,R)-2,4-pentanediol acetal as a colorless oil in 75% yield (85 mg, 12 mmol); 5:1 endo:exo; 90% ee. Product ratios were determined by GLC (Bodman Γ-TA column, 70° C. initial temp, 3° C./min gradient, 23 psi) $t_r$=24.0 min and 24.9 min. $^1H$ NMR, $^{13}C$ NMR, and IR data were consistent with previously published spectra (see Ishihara et al. (1998), supra).

EXAMPLE 12

Preparation of (1R, 2S)-Acetic acid 6-formyl-cyclohex-2-enyl ester (Table 3, entry 6):

To a solution of 5 (27 mg, 0.11 lmmol) and 1,4-dimethoxybenzene (50 mg, 0.36 mmol) in $CF_3OH/H_2O$ (95/5 v/v) was added acrolein (214 μL, 3.21 mmol) followed by 1-acetoxybutadiene (127 μL, 1.07 mmol). The resulting solution was stirred until the diene was consumed (GLC analysis, CC-1701 column, 50° C. isotherm for 10 min, then 50° C./min to 240° C. isotherm, 25 psi); cis-1-acetoxybutadiene $t_r$=4.5 min, trans-1-acetoxybutadiene $t_r$=4.7 min, cyclohexa-1,3-dienecarbaldehyde $t_r$=12.0 min, 1,4-dimethoxybenzene $t_r$=13.0 min, trans-acetic acid 6-formyl-cyclohex-2-enyl ester $t_r$=13.7 min, cis-acetic acid 6-formyl-cyclohex-2-enyl ester $t_r$=13.8 min. A GLC yield of 72% was determined by comparison of the peak areas of acetic acid 6-formyl-cyclohex-2-enyl ester and 1,4-dimethoxybenzene; 85% ee. $^1H$ NMR, $^{13}C$ NMR, and IR data were consistent with previously reported value (Gouesnard et al. (1974) Tetrahedron 30:151. Enantiomeric excess was determined by GLC analysis using a Bodman Γ-TA column (100° C., 1 mL/min) $t_r$=34.0 min and 47.9 min.

EXAMPLE 13

Enantioselectivity Studies:

The capacity of chiral amines to enantioselectively catalyze the Diels-Alder reaction bewteen α,β-unsaturated aldehydes and various dienes was evaluated. The proposed mechanism for the reaction is outlined in Scheme 1. As shown therein, the condensation of aldehyde (1) with an enantiopure amine results in the formation of activated iminium ion (2), which in turn engages a diene reaction partner. Accordingly, Diels-Alder cycloaddition would lead to the formation of an iminium ion (3), which upon hydrolysis would provide the enantio-enriched cycloaddition product (4) while reconstituting the chiral amine catalyst.

Scheme 1

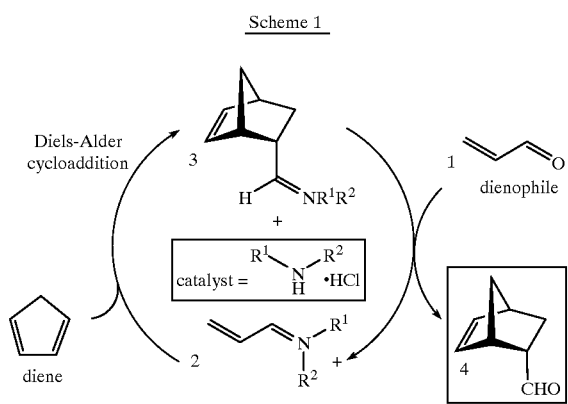

Catalyst:

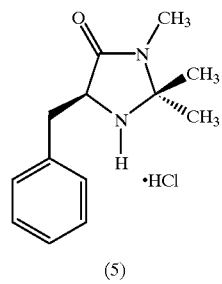

(5)

The enantio selective catalytic Diels-Alder strategy was first evaluated using cyclopentadiene with (E)-cinnemaldehyde and a series of chiral secondary amnine HCl salts. As revealed in Table 1, this LUMO lowering strategy was successful using catalytic quantities (10 mol%) of both (S)proline and (S)aberine derived methyl esters providing the Diels-Alder adduct in excellent yield and moderate stereoselectivity (Table 1, entries 1 and 2, >80%, exo:endo 2.3–2.7: 1, 48–59% ee). In an effort to increase the enantiofacial discrimination of the cycloaddition step, a catalyst was then designed in order to enforce high levels of stereocontrol in the formation of the iminium ion. High levels of enantioselectivity (92% ee) and catalyst efficiency (5 mol%) displayed by imidazolidinone salt 5 to provide the Diels-Alder adduct in 90% yield (entry 3) confirm the utility of such an amine salt as an optimal organic catalyst.

TABLE 1

Organocatalyzed Diels-Alder Reaction between Cinnemaldehyde and Cyclopentadiene

| entry | catalyst | Time (h) | % yield | exo:endo | exo ee (%) |
|---|---|---|---|---|---|
| 1 | (S)-Pro-OMe.HCl | 27 | 81 | 2.7:1 | 48 (2R) |
| 2 | (S)-Abr-OMe.HCl | 10 | 80 | 2.3:1 | 59 (2S) |
| 3 | 5 | 8 | 99 | 1.3:1 | 93 (2S) |

Subsequent experiments that probed the scope of the dienophile reaction component are summarized in Table 2. Variation in the steric contribution of the olefin substituent ($R_1$=Me, Pr, i-Pr entries 1–3) was found without loss in yield or enantioselectivity (>75% yield, endo ee >90%, exo ee >84%). The dienophile component was also tolerant of aromatic groups on the dienophile (entries 4–5, 89% yield, endo ee >93%, exo ee >91%). To confirm the preparative utility of the methodology, the addition of cyclopentadiene to cinnamaldehyde was performed on a 50-mmol scale utilizing catalyst 5.

TABLE 2

Organocatalyzed Diels-Alder Cycloadditions between Cyclopentadiene and Representative Dienophiles

| entry | R | Time (h) | % yield | exo:endo | exo ee (%) | endo ee (%) |
|---|---|---|---|---|---|---|
| 1 | Me | 16 | 75 | 1:1 | 86 (2S) | 90 (2S) |
| 2 | Pr | 14 | 92 | 1:1 | 86 (2S) | 90 (2S) |
| 3 | i-Pr | 14 | 81 | 1:1 | 84 (2S) | 93 (2S) |
| 4 | Ph | 21 | 99 | 1.3:1 | 93 (2S) | 93 (2S) |
| 5 | Furyl | 24 | 89 | 1:1 | 91 (2S) | 93 (2S) |

This amine-catalyzed Diels-Alder cyclo addition was also general with respect to diene structure (Table 3). As revealed with 1,3-diphenylisobenzofuran and cyclohexadiene (entries 1 and 2), a range of diene structures could be used without loss in stereocontrol (entry 1, 75% yield, 35:1 exo: endo, 96% ee; entry 2, 82% yield, 1:14 exo:endo, 94% ee). This methodology allows access to a number of cyclohexenyl building blocks that incorporate acetoxy, alkyl, formyl and aryl substituents with high levels of regio-, diastereo- and enantioselectivity (entries 3–6, 72–89% yield, 1:5–1:11 exo:endo, 83–90% ee). It should also be noted that the reactions depicted in Tables 2 and 3 were performed under an aerobic atmosphere, using wet solvents and an inexpensive, bench-stable catalyst, further emphasizing the preparative advantages of the methods and compositions of the invention.

TABLE 3

Organocatalyzed Diels-Alder Cycloadditions between Acrolein or Crotonaldehyde and Representative Dienes

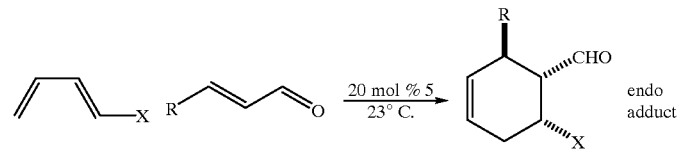

| entry | diene | R | product | yield | exo:endo | % ee |
|---|---|---|---|---|---|---|
| 1 | 1,3-diphenylisobenzofuran | Me | | 75 | 35:1 | 96[c] |
| 2 | cyclohexadiene | H | | 82 | 1:14 | 94[d] |
| 3 | isoprene | H | | 84 | — | 89 |

TABLE 3-continued

Organocatalyzed Diels-Alder Cycloadditions between Acrolein or Crotonaldehyde and Representative Dienes

| entry | diene | R | product | yield | exo:endo | % ee |
|---|---|---|---|---|---|---|
| 4 | Ph | H | Ph | 90 | — | 83 |
| 5 | | Me | | 75 | — | 90 |
| 6 | Me, Me | H | Me, Me | 75 | 1:5 | 90 |
| 7 | OAc | H | OAc | 72 | 1:11 | 85 |

Enantioselective formation of the (R)-formyl Diels-Alder adduct was observed in all cases involving the imidazolidinone catalyst 5, and was consistent with the calculated iminium ion model MM3–9 (a Monte-Carlo simulation using the MM3 force-field; Macromodel V6.5). Inspection of structure MM3–9 reveals two salient stereocontrol elements: (i) the enforced fornation of the (E)-iminium isomer to avoid non-bonding interactions between the appendant olefin and the sterically encumbered dimethyl-bearing carbon and (ii) the bulky benzyl group on the catalyst framework which effectively shields the Re-face of the unsaturated iminium ion, leaving the Si-face exposed to cycloaddition.

What is claimed is:

1. A catalyst composition comprising a chiral imidazolidinone and an acid that ionically associate to form a chiral imidazolidinone salt, wherein the acid is selected from the group consisting of an inorganic Bronsted acid and a carboxylic acid, and the molar ratio of the acid to the chiral imidazolidinone is greater than 1:1 and less than 100:1, such that the composition contains an excess of the acid in addition to the chiral imidazolidinone salt.

2. The composition of claim 1, wherein the molar ratio is less than 20:1.

3. The composition of claim 2, wherein the molar ratio is less than 2:1.

4. The composition of claim 1, wherein the chiral imidazolidinone salt is covalently bound, directly or indirectly, to a solid support.

5. The catalyst composition of claim 1, wherein the acid is an inorganic Bronsted acid.

6. The catalyst composition of claim 5, wherein the inorganic Bronsted acid is selected from the group consisting of hydrochloric acid, hydrobromic acid, sulfurous acid, sulfuric acid, sulfonic acids, nitric acid, nitrous acid, perchloric acid, chromic acid, fumaric acid, maleic acid, succinic acid phosphonic acids, phosphoric acid, and mixtures thereof.

7. The catalyst composition of claim 1, wherein the acid is a carboxylic acid.

8. The catalyst composition of claim 7, wherein the carboxylic acid has the structural formula (V)

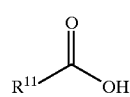

(V)

wherein $R_{11}$ is aryl, alkyl, substituted aryl or substituted alkyl.

9. The catalyst composition of claim 1, wherein the chiral imidazolidinone has the structure

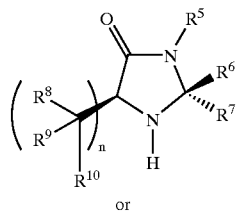

or

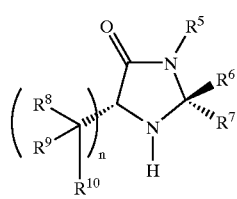

wherein:
$R^5$, $R^6$ and $R_7$ are independently selected from the group consisting of hydroxyl, $C_1$–$C_{30}$ hydrocarbyl, and substituted $C_1$–$C_{30}$ hydrocarbyl;

$R^8$ and $R^9$ are independently selected from the group consisting of hydrido, halo hydroxyl, $C_1$–$C_{30}$ hydrocarbyl, and substituted $C_1$–$C_{30}$ hydrocarbyl, or wherein any two or more of $R^5$, $R^6$, $R^7$, $R^8$ and R9 may be linked together to form a $C_1$–$C_{30}$ hydrocarbylene or substituted $C_1$–$C_{30}$ hydrocarbylene bridge;

n is 1; and $R^{10}$ is a cyclic group, either unsubstituted or substituted with substituents that may be the same or different and are selected from the group consisting of halo, hydroxyl, $C_1$–$C_{30}$ hydrocarbyl, and substituted $C_1$–$C_{30}$ hydrocarbyl, wherein the imidazolidinone is optionally covalently bound, directly or indirectly, to a solid support.

10. The catalyst composition of claim 9, wherein the chiral imidazolidinone has the structure 11. The catalyst composition of claim 9, wherein the chiral imidazolidinone has the structure 12. The catalyst composition of claim 9, where $R^5$, $R^6$ and $R^7$ are independently selected from the group consisting of hydroxyl, $C_1$–$C_{24}$ alkyl, substituted $C_1$–$C_{24}$ alkyl, heteroatom-containing $C_1$–$C_{24}$ alkyl, $C_2$–$C_{24}$ alkenyl, substituted $C_2$–$C_{24}$ alkenyl, $C_2$–$C_{24}$ alkynyl, substituted $C_2$–$C_{24}$ alkynyl, aryl, and substituted aryl;

$R^8$ and $R^9$ are hydrido; and n is 1; and $R^{10}$ is an unsubstituted phenyl group.

13. The catalyst composition of claim 12, wherein $R^5$, $R^6$ and $R^7$ are $C_1$–$C_{24}$ alkyl.

14. The catalyst composition of claim 12, wherein $R^5$, $R^6$ and $R^7$ are lower alkyl.

15. The catalyst composition of claim 12, wherein $R^5$, $R^6$ and $R^7$ are methyl.

16. A reaction system comprising: (a) a substrate having the structural formula (I)

(I)

wherein FG comprises a functional group, $R^1$ is hydrido, hydrocarbyl, substituted hydrocarbyl, heteroatom-comtaining hydrocarbyl, substituted heteroatom-containing hydrocarbyl or silyl and is optionally covalently bound, directly or indirectly or indirectly, to FG, and $Q^1$ and $Q^2$ are independently selected from the group consisting of $OR^1$, $SR^1$, $N(R^1)_2$, $NR^1(OR^1)$, $NR^1(SR^1)$, and $NR^1$—$N(R^1)_2$, or $Q^1$ and $Q^2$ together form =Q in which Q is O, S, $NR^1$, $N(OR^1)$, $N(SR^1)$, an N—$N(R^1)_2$; and (b) a catalyst composition comprising a salt of a chiral imidazolidinone and an acid selected from the group consisting of an inorganic Bronsted acid and a carboxylic acid.

17. The reaction system of claim 16, wherein the imidazolidinone is covalently bound, directly or indirectly, to a solid support.

18. The reaction system of claim 16, wherein FG contains a π bond between two atoms that are α and β to the carbon atom bound to $Q^1$ and $Q^2$.

19. The reaction system of claim 18, wherein FG comprises A=B or A≡B wherein A is C or N and B is N, C or O.

20. The reaction system of claim 19, wherein FG comprises C=C, C=C=C, C≡C, C=N, C≡N, C=O or C=S.

21. The reaction system of claim 20, where FG is alkenyl and $Q^1$ and $Q^2$ together form =O, such that the first reactant is an α,β-unsaturated carbonyl compound.

22. The reaction system of claim 16, wherein the acid is an inorganic Bronsted acid.

23. The reaction system of claim 22, wherein the inorganic Bronsted acid is selected from the group consisting of hydrochloric acid, hydrobromic acid, sulfurous acid, sulfuric acid, sulfonic acids, nitric acid, nitrous acid, perchloric acid, chromic acid, fumaric acid, maleic acid, succinic acid phosphonic acids, phosphoric acid, and mixtures thereof.

24. The reaction system of claim 16, wherein the acid is a carboxylic acid.

25. The reaction system of claim 24, wherein the carboxylic acid has the structural formula (V)

(V)

wherein $R^{11}$ is aryl, alkyl, substituted aryl or substituted alkyl.

26. The reaction system of claim 16, wherein the chiral imidazolidinone has the structure or wherein:

$R^5$, $R^6$ and $R^7$ are independently selected from the group consisting of hydroxyl, $C_1$–$C_{30}$ hydrocarbyl, and substituted $C_1$–$C_{30}$ hydrocarbyl;

$R^8$ and $R^9$ are independently selected from the group consisting of hydrido, halo hydroxyl, $C_1$–$C_{30}$ hydrocarbyl, and substituted $C_1$–$C_{30}$ hydrocarbyl, or wherein any two or more of $R^5$, $R^6$, $R^7$, $R^8$ and $R^9$ may be linked together to form a $C_1$–$C_{30}$ hydrocarbylene or substituted $C_1$–$C_{30}$ hydrocarbylene bridge;

n is 1; and $R^{10}$ is a cyclic group, either unsubstituted or substituted with substituents that may be the same or different and are selected form the group consisting halo, hydroxyl, $C_1$–$C_{30}$ hydrocarbyl, and substituted $C_1$–$C_{30}$ hydrocarbyl, wherein the imidazolidinone is optionally covalently bound, directly or indirectly, to a solid support.

27. The reaction system of claim 26, wherein the chiral imidazolidinone has the structure

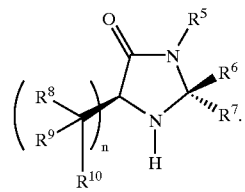

28. The reaction system of claim 26, wherein the chiral imidazolidinone has the structure

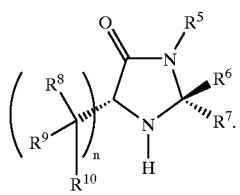

29. The reaction system of claim 26, wherein $R^5$, $R^6$ and $R^7$ are independently selected from the group consisting of hydroxyl, $C_1$–$C_{24}$ alkyl, substituted $C_1$–$C_{24}$ alkyl, heteroatom-containing $C_1$–$C_{24}$ alkyl, $C_2$–$C_{24}$ alkenyl, substituted $C_2$–$C_{24}$ alkenyl, $C_2$–$C_{24}$ alkynyl, substituted $C_2$–$C_{24}$ alkynyl, aryl, and substituted aryl;

$R^8$ and $R^9$ are hydrido; and n is 1; and $R^{10}$ is an unsubstituted phenyl group.

30. The reaction system of claim 21, wherein $R^5$, $R^6$ and $R^7$ are $C_1$–$C_{24}$ alkyl.

31. The reaction system of claim 30, wherein $R^5$, $R^6$ and $R^7$ are lower alkyl.

32. The reaction system of claim 31, wherein $R^5$, $R^6$ and $R^7$ are methyl.

33. The reaction system of claim 16, wherein the catalyst composition further comprises an excess of the acid.

34. The reaction system of claim 33, wherein the molar ratio of the acid to the chiral imidazolidinone in the catalyst composition is greater than 1:1 and less than 100:1.

35. The reaction system of claim 34, wherein the molar ratio is less than 20:1.

36. The reaction system of claim 35, wherein the molar ratio is less than 2:1.

* * * * *

UNITED STATES PATENT AND TRADEMARK OFFICE
CERTIFICATE OF CORRECTION

PATENT NO. : 6,534,434 B2  
DATED : March 18, 2003  
INVENTOR(S) : David W.C. MacMillan et al.

It is certified that error appears in the above-identified patent and that said Letters Patent is hereby corrected as shown below:

Column 28,  
Line 43, please delete "$R_{11}$" and replace with -- $R^{11}$ --.  
Line 65, please delete "$R_7$" and replace with -- $R^7$ --.

Column 29,  
Line 4, please delete "R9" and replace with -- $R^9$ --.  
Line 65, please delete "comtaining" and replace with -- containing --.  
Line 67, please delete "or indirectly of indirectly" and replace with -- or indirectly --.

Column 31,  
Line 12, please delete "form" and replace with -- from --.  
Line 12, please delete "consisting halo" and replace with -- consisting of halo --.

Column 32,  
Line 18, please delete "claim 21" and replace with -- claim 29 --.

Signed and Sealed this

Twenty-ninth Day of July, 2003

JAMES E. ROGAN  
*Director of the United States Patent and Trademark Office*